United States Patent
Ekelund

(10) Patent No.: US 9,682,101 B2
(45) Date of Patent: Jun. 20, 2017

(54) COMPOSITION FOR THE TREATMENT OF DISEASE

(71) Applicant: FERRING B.V., Hoofddorp (NL)

(72) Inventor: Mats Ekelund, Lund (SE)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 14/779,412

(22) PCT Filed: Mar. 25, 2014

(86) PCT No.: PCT/EP2014/055937
§ 371 (c)(1),
(2) Date: Sep. 23, 2015

(87) PCT Pub. No.: WO2014/154677
PCT Pub. Date: Oct. 2, 2014

(65) Prior Publication Data
US 2016/0051578 A1    Feb. 25, 2016

(30) Foreign Application Priority Data

Mar. 25, 2013 (EP) ..................................... 13160799
Sep. 20, 2013 (WO) ................. PCT/EP2013/069570

(51) Int. Cl.
| A61K 33/00 | (2006.01) |
| A61K 9/00 | (2006.01) |
| A61K 9/28 | (2006.01) |
| A61K 9/50 | (2006.01) |
| A61K 33/44 | (2006.01) |
| A61K 9/48 | (2006.01) |
| C01B 31/08 | (2006.01) |
| A61K 45/06 | (2006.01) |
| A61K 9/20 | (2006.01) |

(52) U.S. Cl.
CPC ............ *A61K 33/00* (2013.01); *A61K 9/0031* (2013.01); *A61K 9/0053* (2013.01); *A61K 9/0095* (2013.01); *A61K 9/2886* (2013.01); *A61K 9/4816* (2013.01); *A61K 9/5026* (2013.01); *A61K 9/5042* (2013.01); *A61K 9/5047* (2013.01); *A61K 9/5073* (2013.01); *A61K 33/44* (2013.01); *A61K 45/06* (2013.01); *C01B 31/08* (2013.01); *A61K 9/2081* (2013.01)

(58) Field of Classification Search
None
See application file for complete search history.

(56) References Cited

U.S. PATENT DOCUMENTS

| 4,406,896 A * | 9/1983 | Higuchi ................... A61K 9/02 514/161 |
| 5,554,370 A * | 9/1996 | Uehara ................... A61K 33/40 424/125 |
| 5,644,011 A * | 7/1997 | Lehmann ............. A61K 9/5026 526/317.1 |
| 5,937,862 A * | 8/1999 | Targan ............. G01N 33/56972 128/898 |
| 6,632,454 B2 * | 10/2003 | Beckert ................ A61K 9/5073 424/439 |
| 7,341,741 B1 * | 3/2008 | Sachetto .............. A61K 9/0031 424/195.18 |
| 2004/0166248 A1 | 8/2004 | Hu et al. |
| 2007/0292509 A1 * | 12/2007 | Tanji ..................... A61K 9/1652 424/470 |
| 2008/0031867 A1 | 2/2008 | Huguet et al. |
| 2008/0254131 A1 | 10/2008 | Vandse et al. |
| 2009/0148538 A1 * | 6/2009 | Fischer .............. A61K 31/4164 424/600 |
| 2009/0214642 A1 * | 8/2009 | Legen .................. A61K 9/5047 424/457 |
| 2010/0008987 A1 * | 1/2010 | Chowdary ........... A61K 31/137 424/472 |
| 2014/0243794 A1 | 8/2014 | Halskov et al. |
| 2015/0245999 A1 | 9/2015 | Halskov |

FOREIGN PATENT DOCUMENTS

| GB | 2 012 257 A | 7/1979 |
| WO | WO 98/22096 A1 | 5/1998 |
| WO | WO 2009/049239 A1 | 4/2009 |
| WO | WO 2011/104275 A1 | 9/2011 |

OTHER PUBLICATIONS

International Search Report issued on Jul. 16, 2014 in application No. PCT/EP2014/055937.
Office Action issued on Jul. 15, 2016 in U.S. Appl. No. 14/429,806 (US 2015/0245999).
Office Action issued on Feb. 11, 2016 in U.S. Appl. No. 14/429,806 (US 2015/0245999).
Office Action issued on Dec. 20, 2016 in U.S. Appl. No. 14/429,806 (US 2015-0245999).

* cited by examiner

*Primary Examiner* — Frederick Krass
*Assistant Examiner* — Celeste A Roney
(74) *Attorney, Agent, or Firm* — Foley & Lardner LLP

(57) ABSTRACT

A composition for use in the treatment of a condition or disorder related to mucosal barrier dysfunction in the gut, the composition comprising activated carbon. The condition may be, for example, pouchitis or proctitis.

23 Claims, 6 Drawing Sheets

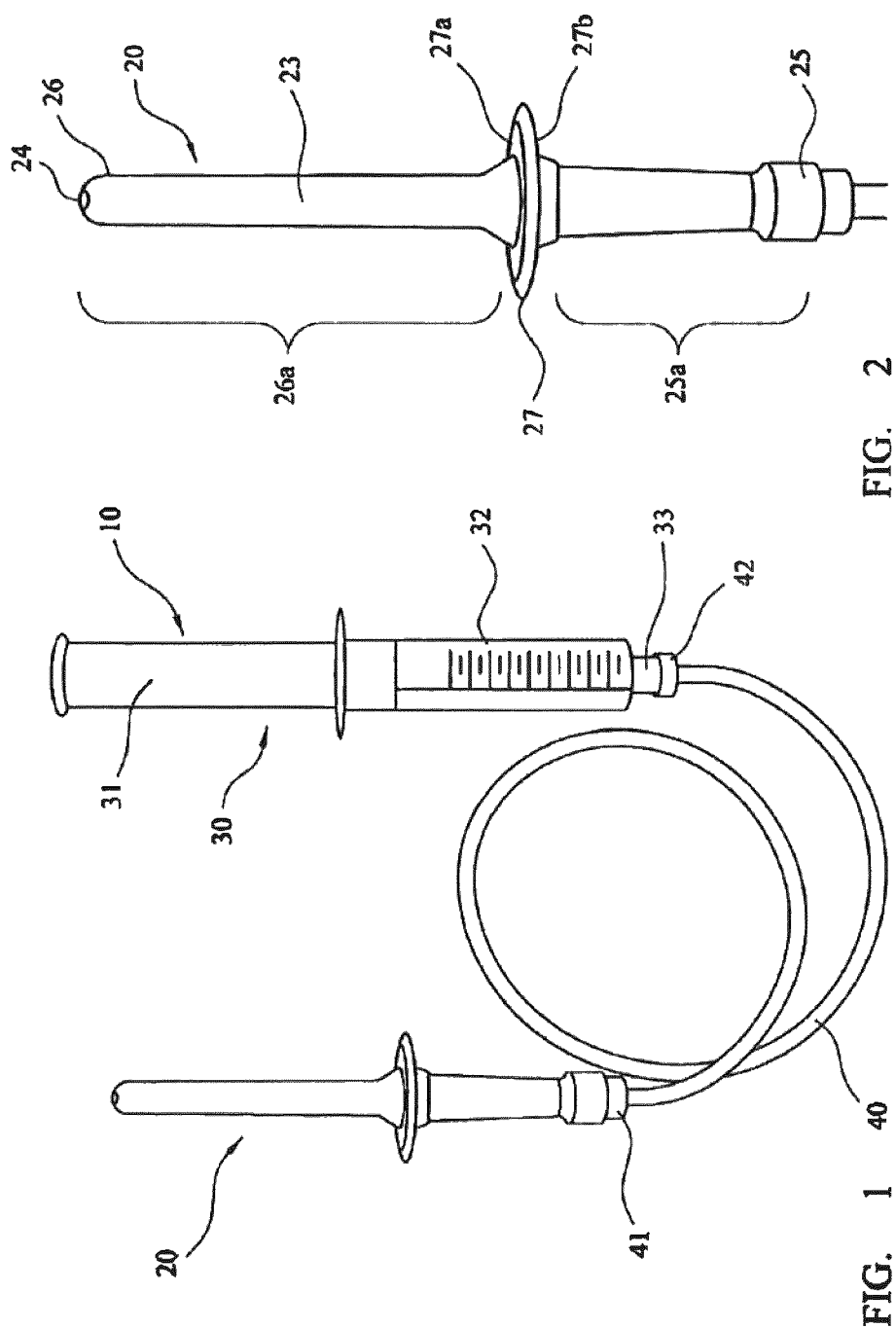

COMPOSITION FOR THE TREATMENT OF DISEASE

The invention relates to a pharmaceutical composition comprising activated carbon particles for the treatment of conditions and disorders related to mucosal barrier dysfunction in the gut (gastrointestinal tract), including proctitis (e.g. radiation proctitis), and/or pouchitis.

BACKGROUND

The main pathophysiologic driver of many gastrointestinal disorders/diseases has been postulated to be translocation, i.e. mucosal barrier dysfunction meaning that the gastrointestinal mucosa becomes leaky and substances that in normal situations should be kept in the lumen of the gut may pass across the gut epithelium into the body. Crohn's disease, ulcerative colitis, and IBS (Irritable bowel syndrome) are examples of diseases in which clear evidence exists that the mucosa integrity is diminished. In patients who have undergone resection of the entire colon and rectum an ileal pouch is constructed in order to replace rectum and provide patients the possibility of more normal bowel habits. The mucosa in this pouch has been shown to leak which may induce an inflammation in the pouch mucosa, known as pouchitis. In peritonitis developing in patients with liver cirrhosis and ascites it has been hypothesized that the bacteria generating the peritonitis actually originates from the gut and are transported to the peritoneal cavity directly through the gut mucosa. Radiation enteritis is induced by radiation therapy and it is believed that the radiation induced mucosal damage disrupts the mucosa, thus allowing for translocation of chemicals as well as bacteria and residues thereof.

It is not known which substances actually leak and are deleterious to the body, although it is plausible to assume that everything that is not actively absorbed in one way or another may be harmful to the body. Such substances include bacteria and viruses, residues of bacteria (LPS), bile acids (unless they have been actively absorbed and properly handled by the epithelial cells), toxins produced by bacteria, and food substances that should not be absorbed.

Treatment of the conditions mentioned above has so far been focused on the complications induced by the translocation, such as inflammation, infection, diarrhea induced dehydration, etc. Much effort in research has been devoted to find treatments to strengthen the mucosal barrier, yet without any significant progress. Another treatment modality is to take care of the potential lethal substances before they enter the gut lumen or within the gut lumen before they enter the gut mucosa. The absolutely most successful drug globally today is therefore pure water which prevents people from getting cholera and other diseases transmitted via decontaminated water. However, most of the above mentioned conditions/diseases are obviously not due to decontaminated water and thus require other treatment modalities.

Proctitis may be defined as an isolated inflammation of the anorectal area (e.g. the anus and the lining of the rectum, generally affecting only the last 6 inches of the rectum).

There are many causes of proctitis, but they can generally be grouped in the following categories: Autoimmune disease; Harmful substances and radiation; Non-sexually transmitted infection; and Sexually transmitted disease (STD).

Proctitis caused by STD is common among those who engage in anal intercourse. STDs that can cause proctitis include HIV, gonorrhea, herpes, chlamydia, and lymphogranuloma venereum. Non-sexually transmitted infections causing proctitis are seen less often than STD proctitis. The classical example of non-sexually transmitted infection occurs in children and is caused by the same bacteria that cause strep throat. Autoimmune proctitis is associated with diseases such as ulcerative colitis or Crohn's disease. Proctitis may also be caused by certain medications and inserting harmful substances into the rectum.

In addition, proctitis may also be linked to stress and can result from an intolerance to gluten (celiac disease-associated "proctitis")

Symptoms associated with proctitis are e.g. ineffectual straining to empty the bowels, diarrhea, rectal bleeding and possible discharge, a feeling of not having adequately emptied the bowels, involuntary spasms and cramping during bowel movements, left-sided abdominal pain, passage of mucus through the rectum, and anorectal pain. A common symptom is a continual urgency. Another is tenderness and mild irritation in the rectum and anal region. A serious symptom is pus and blood in the discharge, accompanied by cramps and pain during the bowel movement. If there is severe bleeding, a condition called anemia can also be caused, showing symptoms such as pale skin, irritability, weakness, dizziness, brittle nails, and shortness of breath. Proctitis symptoms can be short-lived or become chronic (last for weeks or months or longer) and are associated with great discomfort, reducing the patients quality life.

Radiation proctitis is inflammation and damage to the lower parts of the colon and rectum after exposure to x-rays or other ionizing radiation as a part of radiation therapy. Radiation proctitis most commonly occurs after treatment for cancers such as cervical cancer, prostate cancer, and colon cancer.

Radiation proctitis can generally be classified as acute or chronic, usually delineated by the timeframe of symptoms in relation to the treatment as well as the presenting symptoms and signs. In acute radiation proctitis, the symptoms occur in the first few weeks after therapy. These symptoms include diarrhea and the urgent need to defecate, often with inability to do so (tenesmus). Acute radiation proctitis usually resolves without treatment after several months, but symptoms may improve with butyrate enemas. This acute phase is due to direct damage of the lining (epithelium) of the colon. In chronic radiation proctitis the symptoms may begin as early as several months after therapy but occasionally not until several years later. These symptoms include diarrhea, rectal bleeding, painful defecation, and intestinal blockage. Intestinal blockage is a result of narrowing of the rectum which blocks the flow of feces. Chronic radiation proctitis occurs in part because of damage to the blood vessels which supply the rectum, depriving the rectum of oxygen and necessary nutrients. Proctitis can be diagnosed by looking inside the rectum with a proctoscope or a sigmoidoscope.

Treatment for proctitis varies depending on severity and cause. For example for proctitis caused by bacterial infection antibiotics may be used. If the proctitis is caused by Crohn's disease or ulcerative colitis, 5-aminosalicyclic acid (5-ASA) or corticosteroids may be applied directly to the area in enema or suppository form, or taken orally in pill. Symptoms of radiation proctitis such as diarrhea and painful defecation may be treated with oral opioids and stool softeners, respectively. Complications such as obstruction may require surgery. Several other methods were under development as of 2005 to lessen the effects of radiation proctitis. These include sucralfate, hyperbaric oxygen therapy, corticosteroids, metronidazole, argon plasma coagulation, and radiofrequency ablation. However, medical therapy is often unsuccessful and surgery may eventually be required.

Accordingly, there is a need for additional treatment options either as an alternative treatment or a treatment supplementing current available therapies.

Pouchitis may be defined as inflammation of an ileal pouch (e.g. an artificial rectum surgically created out of ileal gut tissue in patients who have undergone e.g. colectomy). Ileal pouch-anal anastomosis (IPAA) with proctocolectomy is a surgical treatment which may be used in patients with ulcerative colitis where medical treatment is not effective. A proctocolectomy is performed and the remaining ileum is made into a reservoir, or pouch, which is connected to the anus. IPAA avoids a permanent ileostomy and means that the patient can retain stool (in the pouch) and eliminate this in the usual manner, thus improving patient quality of life. However complications can occur. One such complication is pouchitis which is an inflammation of the lining of pouch. Patients with pouchitis may suffer from diarrhoea, abdominal pain, cramps, increased number of bowel movements and a strong feeling of the need to have a bowel movement and pelvic discomfort.

There is presently no approved treatment or cure for pouchitis. First line treatment is usually with antibiotics, for example ciprofloxacin and metronidazole. Administration of antibiotics over a prolonged period can cause various side effects limiting their use. However, pouchitis does not always respond to antibiotic treatment. Indeed, pouchitis can be classified based on the response to antibiotic treatment, and the classifications include antibiotic-responsive pouchitis, antibiotic-dependent pouchitis, and antibiotic refractory pouchitis.

Other therapies include the use of probiotic or drugs used to control an episode of pouchitis and their uses depends on the severity of the flare up. The drugs may be delivered using enemas applied directly into the pouch through the anus or may be given as tablets, or liquids taken by mouth.

In some cases pouchitis becomes chronic and does not respond to treatment and thus it may become necessary to perform another surgical operation. This may be to divert stool away from the pouch, to allow the pouch to rest, or in some severe cases to remove the pouch completely.

There is, therefore, a need for a composition which will treat pouchitis alongside, or as an alternative to, antibiotic or other current treatment therapies.

Activated carbon has been proposed for use in the treatment of pouchitis. US2009/0148538 discloses oral administration of activated carbon to treat pouchitis.

However, orally administered activated carbon must pass through a patient's entire digestive system before it reaches the rectal region and in doing so a large (and unpredictable) proportion of the carbon will have adsorbed various chemicals and lost its activity, or otherwise lost its activity, depending on various factors such as amount of food in gut, inter patient variations and day to day variations. By increasing the dose of orally administered activated carbon it may be possible to increase the proportion of carbon that reaches the rectum in an activated state. However, activated carbon absorbs many essential chemicals and nutrients on passing through the patient's digestive system and the long-term administration of large oral doses of activated carbon over a prolonged period is therefore undesirable and even harmful to the patient.

Activated carbon has been prepared for rectal administration (e.g. as an enema) by pre-mixing to form a suspension with a liquid (e.g. propylene glycol). The problem with such suspensions is that the carbon may lose its activity very quickly due to adsorption of components of the liquid by the activated carbon. For example, experiments have compared the amount of phenazone adsorbed per 100 g activated carbon suspended in either water or 50% water/propylene glycol. The results showed that in water, activated carbon adsorbed 43 g phenazone per 100 g carbon; in 50% propylene activated carbon adsorbed only 16 g per 100 g phenazone. Clearly, the activity of the carbon is markedly reduced by adsorption of the propylene glycol. Suspensions of activated carbon, therefore, need to be used shortly after preparation and have little practical shelf-life.

Activated carbon has also been coated or otherwise formulated to allow it to pass through a patient's digestive system when taken orally. For example, U.S. Pat. No. 5,554,370 discloses capsules for oral administration of activated carbon. It may be difficult to prepare a coating that accurately dissolves to release the activated carbon only once it has passed into a patient's rectum. Furthermore, such coating or encapsulation may itself reduce or eliminate the activity of the carbon (e.g. in the same manner as described above for suspensions) and thereby may reduce the effectiveness of such coated particles.

JP2005-089306 discloses a suppository comprising activated carbon. The suppository is formulated with other excipients (e.g. gelatine, wax such as Witepsol W35) which effectively coat the activated carbon. As discussed above, coating reduces or eliminates the activity of the carbon and thereby may reduce the effectiveness of such coated particles. Further, suppositories which include activated carbon may not achieve predictable or effective administration of activated carbon particles for several reasons. Firstly, administration by suppository requires effective insertion by the patient to the required depth, which is not always achieved, and may be unhygienic. Further, therapeutic benefit requires effective capillary flow of activated carbon particles from the rectal cavity which may not be achieved because of the weight of the activated carbon particles and/or inter-patient variation of mucosal secretion; the activated carbon may remain at the base of the rectum and therefore not reach the site of activity. Thus, suppositories including activated carbon are far from ideal. JP2005-089306 also discloses an example of an enema formulation. However, as indicated above, enema suspensions tend to have poor shelf life and reduced activity due to adsorption of components of the liquid by the activated carbon. The inclusion of preservatives in enema suspensions of activated carbon (e.g. suspensions in water) to enhance shelf life is inappropriate because the preservative would be adsorbed by the activated carbon, thereby reducing activity of the activated carbon and leaving the water phase unprotected.

Thus, there is a need for compositions for (use in) the treatment of pouchitis and proctitis which retain their pharmaceutical activity prior to administration (i.e. have good shelf life), have improved handling qualities, and are associated with predictable and repeatable dosing and good patient compliance.

The applicants have surprisingly found that it is possible to formulate and administer activated carbon which is dust free [for example activated carbon of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm)], as a dry powder or dry dose. Formulation of activated carbon as a dry powder prevents deactivation of the carbon (there is no adsorption of other excipients or components of the administration vehicle on the activated carbon); allows effective administration without the problems associated with rectal suppositories and oral administration (particles of this size may be administered rectally as a powder, and there is little or no loss of activity due to adsorption in the gut); and has other advantages in terms of cleanliness and contamination (particles of this size are not dusty).

According to the present invention there is provided a composition for (use in) the treatment of a condition or disorder related to mucosal barrier dysfunction in the gut (gastrointestinal tract), the composition comprising activated carbon. The condition or disorder related to mucosal barrier dysfunction in the gut may be caused by translocation (i.e. caused by leaking in the gastrointestinal mucosa such that substances that should remain in the lumen of the gut pass across the gut epithelium into the body). The condition or disorder related to mucosal barrier dysfunction in the gut may be proctitis (including radiation proctitis), pouchitis, ulcerative colitis, Crohns disease, IBS, ascites (associated with liver cirrhosis), pancreatitis or radiation enteritis.

The composition comprising activated carbon may be for oral administration and comprise:
(a) a core comprising activated carbon (e.g. activated carbon as the sole active pharmaceutical ingredient);
(b) a first (e.g. an inner) layer around (e.g. surrounding) the core, the first layer comprising an insoluble semipermeable material; and
(c) a second (e.g. outer) layer around (e.g. surrounding) the first layer which breaks down rapidly (dissolves) at a predetermined pH (e.g. a layer which breaks down rapidly (dissolves) at pH 5 to pH 7, e.g. a layer which breaks down rapidly (dissolves) at pH 5, a layer which breaks down rapidly (dissolves) at pH≥5.5, a layer which dissolves at pH 7 etc.) and/or which dissolves at a predetermined location in the gastrointestinal tract. The components (a), (b) and (c) may be as described herein. The composition for oral administration may be in the form of a powder, suspension, tablet, capsule etc.

The composition comprising activated carbon may be for rectal administration and comprise a dry powder (a dry dose) of activated carbon of particle size 0.001 to 1 mm, for example 0.01 to 1 mm, for example 0.02 to 1 mm.

According to the present invention in a first aspect, there is provided a composition (e.g. a pharmaceutical composition) for (or for use in) the treatment of proctitis (e.g. radiation proctitis), the composition comprising activated carbon. The composition may be for rectal administration. The composition may be for oral administration.

According to the present invention in another aspect there is provided a method of treatment of proctitis comprising a step of administering (to a subject in need thereof) a pharmaceutically effective amount of a composition comprising activated carbon. The administration may be oral or rectal.

According to the present invention in one aspect, there is provided a composition (e.g. a pharmaceutical composition) for use in the treatment of proctitis, the composition comprising a dry powder (a dry dose) of activated carbon which is dust free. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm).

According to the present invention in an aspect there is provided a composition (e.g. a pharmaceutical composition) for use in the treatment of proctitis, the composition comprising a dry powder (a dry dose) of activated carbon of particle size 0.001 to 1 mm, for example 0.01 to 1 mm, for example 0.02 to 1 mm. Preferably, the activated carbon is of particle size 0.05 to 1 mm, for example 0.1 to 0.5 mm, for example 0.15 mm to 0.4 mm, for example 0.2 to 0.3 mm. The activated carbon may be of particle size 0.15 to 1 mm. Preferably the activated carbon is of average particle size 0.05 to 1 mm. Preferably the activated carbon is of average particle size 0.15 to 0.3 mm. Preferably the composition (e.g. pharmaceutical composition) is for use in the treatment of radiation proctitis. Preferably the dry powder (dry dose) of activated carbon is free of dust or substantially free of dust.

According to the present invention in a further aspect there is provided a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm) for use in the treatment of proctitis, or for use in the manufacture of a medicament for the treatment of proctitis. The activated carbon may be of particle size 0.05 to 1 mm. Preferably the activated carbon is of particle size 0.15 to 0.3 mm. The activated carbon may be of average particle size 0.15 to 1 mm. Preferably the dry powder (dry dose) of activated carbon is free of dust or substantially free of dust.

According to the invention in an aspect there is provided a composition for use in the treatment of proctitis, the composition comprising a dry powder of activated carbon of particle size 0.001 to 1 mm, for example 0.02 to 1 mm, preferably 0.05 to 1 mm, wherein the composition is for administration (to be administered) rectally as a dry powder. The activated carbon may be of particle size 0.15 to 1 mm. The activated carbon may be of average particle size 0.15 mm to 0.3 mm.

According to the invention in an aspect there is provided a composition for use in the treatment of proctitis, the composition comprising a dry powder of activated carbon of particle size which is dust free, wherein the composition is for administration (to be administered) rectally as a dry powder. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm).

The composition or dry dose may further comprise an antibiotic, an anti-inflammatory [e.g 5-aminosalicyclic acid (5-ASA)] or a corticosteroid and/or be for administration with an antibiotic, an anti-inflammatory [e.g 5-aminosalicyclic acid (5-ASA)] or a corticosteroid.

According to the present invention in another aspect there is provided a method of treatment of proctitis comprising a step of administering (to a subject in need thereof) a pharmaceutically effective amount of a composition comprising a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm). The activated carbon may be of particle size 0.15 to 1 mm. Preferably the activated carbon is of particle size 0.15 to 0.3 mm. The method may further comprise administering (to a subject in need thereof) a pharmaceutically effective amount of an antibiotic, 5-aminosalicyclic acid (5-ASA) or corticosteroid. According to the present invention in another aspect, there is provided a composition (e.g. a pharmaceutical composition) for (or for use in) the treatment of pouchitis, the composition comprising activated carbon. The composition may be for rectal administration. The composition may be for oral administration.

According to the present invention in another aspect there is provided a method of treatment of pouchitis comprising a step of administering (to a subject in need thereof) a pharmaceutically effective amount of a composition comprising activated carbon. The administration may be oral or rectal.

According to the present invention in one aspect, there is provided a composition (e.g. a pharmaceutical composition) for use in the treatment of pouchitis, the composition comprising a dry powder (a dry dose) of activated carbon which is dust free. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm). Preferably the composition is for rectal administration.

According to the present invention in an aspect there is provided a composition (e.g. a pharmaceutical composition) for use in the treatment of pouchitis, the composition comprising a dry powder (a dry dose) of activated carbon of particle size 0.001 to 1 mm, for example 0.01 to 1 mm, for example 0.02 to 1 mm. Preferably, the activated carbon is of particle size 0.05 to 1 mm, for example 0.1 to 0.5 mm, for example 0.15 mm to 0.4 mm, for example 0.2 to 0.3 mm. The activated carbon may be of particle size 0.15 to 1 mm. Preferably the activated carbon is of average particle size 0.05 to 1 mm. Preferably the activated carbon is of average particle size 0.15 to 0.3 mm. Preferably the dry powder (dry dose) of activated carbon is free of dust or substantially free of dust. Preferably the composition is for rectal administration.

According to the present invention in a further aspect there is provided a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm) for use in the treatment of pouchitis, or for use in the manufacture of a medicament for the treatment of pouchitis. The activated carbon may be of particle size 0.05 to 1 mm. Preferably the activated carbon is of particle size 0.15 to 0.3 mm. The activated carbon may be of average particle size 0.15 to 1 mm. Preferably the dry powder (dry dose) of activated carbon is free of dust or substantially free of dust.

According to the invention in an aspect there is provided a composition for use in the treatment of pouchitis, the composition comprising a dry powder of activated carbon of particle size 0.001 to 1 mm, for example 0.02 to 1 mm, preferably 0.05 to 1 mm, wherein the composition is for administration (to be administered) rectally as a dry powder. The activated carbon may be of particle size 0.15 to 1 mm. The activated carbon may be of average particle size 0.15 mm to 0.3 mm.

According to the invention in an aspect there is provided a composition for use in the treatment of pouchitis, the composition comprising a dry powder of activated carbon of particle size which is dust free, wherein the composition is for administration (to be administered) rectally as a dry powder. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm).

The composition or dry dose may further comprise an antibiotic or probiotic and/or be for administration with an antibiotic or probiotic.

According to the present invention in another aspect there is provided a method of treatment of pouchitis comprising a step of administering (to a subject in need thereof) a pharmaceutically effective amount of a composition comprising a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm). The activated carbon may be of particle size 0.15 to 1 mm. Preferably the activated carbon is of particle size 0.15 to 0.3 mm.

The method may further comprise administering (to a subject in need thereof) a pharmaceutically effective amount of an antibiotic or a probiotic. In aspects of the invention, the composition (e.g. pharmaceutical composition) may comprise a dry powder (dry dose) of activated carbon. Herein the terms "dry dose" and "dry powder" of activated carbon mean activated carbon that has been maintained in dry conditions until the point of delivery to the patient's body. The use of a dry powder (dry dose) of activated carbon particles means the adsorbtive capacity of the activated carbon is retained and maintained until administration.

Preferably the composition or pharmaceutical composition is for rectal administration. The composition or pharmaceutical composition may comprise 450 μg to 10 g activated carbon (to treat pouchitis or proctitis). Preferably the composition or pharmaceutical composition comprises 450 μg to 5 g activated carbon. In an example, the composition or pharmaceutical composition comprises 450 μg to 1 g activated carbon. In another example, the composition or pharmaceutical composition comprises 950 μg to 2.5 g activated carbon. In another example, the composition or pharmaceutical composition comprises 950 μg to 1.3 g activated carbon. In an example the composition or pharmaceutical composition comprises 1.2 g activated carbon. In an example the composition or pharmaceutical composition comprises 1.2 g (±10%) activated carbon. In other words, the composition or pharmaceutical composition may comprise 1.08 to 1.32 g activated carbon.

The composition or pharmaceutical composition may comprise a dose (e.g. a unit dose or single dose) of 450 μg to 10 g activated carbon (to treat pouchitis or proctitis). Preferably the composition or pharmaceutical composition comprises a dose (e.g. a unit dose or single dose) of 450 μg to 5 g activated carbon. In an example, the composition or pharmaceutical composition comprises a dose (e.g. a unit dose or single dose) of 450 μg to 1 g activated carbon. Doses of 450 μg to 1 g activated carbon may be suitable for the treatment of children. In another example, the composition or pharmaceutical composition comprises a dose (e.g. a unit dose or single dose) of 950 μg to 2.5 g activated carbon. In another example, the composition or pharmaceutical composition comprises a dose (e.g. a unit dose or single dose) of 950 μg to 1.3 g activated carbon. Doses of 950 μg to 2.5 g (e.g. of 950 μg to 1.3 g, e.g. doses of 1.1 g, 1.2 g etc.) activated carbon may be suitable for the treatment of adults. Preferably the composition or pharmaceutical composition is for administration 1, 2, or 3 times a day at the dose levels above. Preferably the composition or pharmaceutical composition is for administration after the, or each, bowel movement.

The activated carbon may be granular activated carbon.

Herein the term "particle size" means the width at the narrowest point of the activated carbon particle or granule (e.g the diameter for a spherical or roughly spherical particle).

Activated carbon (e.g. granular activated carbon) and its methods of manufacture is well known in the art and is available from, for example, Chemviron Carbon. Preferably the activated carbon is a pharmaceutical or medical grade activated carbon.

Activated carbon is designated by sizes such as 8×20, 20×40, or 8×30. A 20×40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). A U.S. Standard Mesh Size No. 50 sieve has openings of 0.297 mm; a No. 60 sieve has openings 0.251 mm; a No. 70 sieve has openings 0.211 mm; a No. 80 sieve has openings 0.178 mm; a No. 100 sieve has openings 0.152; a No. 120 sieve has openings 0.125 mm, a No. 140 sieve has openings 0.104 mm, and a No. 170 sieve has openings 0.089 mm. A notation for indicating particle size distribution using mesh size is to use + and − designations. A "+" before the sieve mesh indicates the particles are retained by the sieve, while a "−" before the sieve mesh indicates the particles pass through the sieve. This means that typically 90% or more of the particles will have mesh sizes between the two values. Thus, if the particle size of a material is described as −80/+170 (or could also be written −80+170), then 90% or more of the material will pass through an 80 mesh sieve and be retained by a 170 mesh sieve. Using the figures above, it can be seen that the resulting particles will have a range of diameters between 0.089 and 0.178 mm (89 and 178 micrometers). The activated carbon may be of particle size distribution −50/+120, wherein 90% or more of the activated carbon particles have diameter in the range from 0.125 mm to 0.297 mm. Preferably the activated carbon is of particle size distribution −50/+100, wherein 90% or more of the activated carbon particles have diameter in the range from 0.152 mm to 0.297 mm. Preferably the activated carbon is of particle size distribution −50/+80, wherein 90% or more of the activated carbon particles have diameter in the range from 0.178 mm to 0.297 mm. More preferably the activated carbon is of particle size distribution −50/+70, wherein 90% or more of the activated carbon particles have diameter in the range from 0.211 mm and 0.297 mm.

The activated carbon may be an activated carbon wherein 85% or more of the activated carbon particles have diameter in the range from 0.089 mm to 0.3 mm. The activated carbon may be activated carbon wherein 85% or more of the activated carbon particles have diameter in the range from 0.104 mm to 0.297 mm. The activated carbon may be activated carbon wherein 85% or more of the activated carbon particles have diameter in the range from 0.125 mm to 0.297 mm. A particularly preferred activated carbon is activated carbon wherein 85% or more of the activated carbon particles have diameter in the range from 0.152 mm to 0.297 mm.

It is preferred that the activated carbon particles are formed by grinding carbon material to the desired size. Ground activated carbon has an irregular particle shape and this irregular shape may be particularly suited to being cleanly delivered (e.g. from a delivery device, as described herein). The activated carbon may be in the form of spheronised or spherical particles. The activated carbon may be coated.

The (pharmaceutical composition) may be delivered into a patient's rectal cavity, e.g. using a device. One suitable device comprises a rectally-insertable cannula having a proximal opening, a distal opening, and a cavity defined through a body of the cannula between the proximal opening and the distal opening for containing the dose of pharmaceutical composition. An openable closure acts to close the proximal opening of the canula. Preferably, the cannula is of length 6 to 8 cm, e.g 7 cm. For example, a one-way valve may act to close the proximal opening of the cannula, or alternatively a suitable closure means such as a frangible seal that ruptures on the application of pressure may be used. A frangible seal, or similar ruptureable closure, could only be used one time, and would need to be replaced if the cannula is to be re-used. The device further comprises an actuation means for driving a volume of fluid (e.g. liquid such as water, or gas such as air) through the one-way valve (or alternative closure means) and the cavity to flush the dose of pharmaceutical composition out of the cavity through the distal opening of the cannula. The actuation means or actuator may comprise a suitable volume of liquid or may be loadable with a suitable volume of liquid for flushing the cavity. For example, the actuation means or actuator may have a chamber for holding a volume of liquid that may be filled with a suitable liquid prior to use of the device. A suitable liquid should be a liquid that does not influence the adsorptive capacity of the carbon and may be water or a medical solution, for example a saline solution. The skilled person will be aware of suitable liquids that can safely be injected into a patient's rectum. In another example, the actuation means or actuator may comprise a suitable volume of gas (e.g air) or may be loadable with a suitable volume of gas (e.g. air).

By containing the pharmaceutical composition within the cavity of the cannula, the activated carbon can be maintained separately from the liquid (if the fluid is a liquid) until the point of delivery; in other words the pharmaceutical composition is a dry dose or dry powder. As the activated carbon (the pharmaceutical composition) is stored in a dry condition it does not lose its activity for a considerable period of time and, therefore, the activity of the carbon particles is high as they are injected into the patient. Preferably, the driving fluid or driving liquid (if the fluid is a liquid) does not mix to a great extent with the activated carbon during delivery but merely forces the activated carbon out of the distal opening of the cannula and into a patient's rectum. The function of the fluid/liquid (e.g. air or water) is to act like a piston to drive the carbon into the patient, and the liquid/fluid may therefore be referred to as a driving liquid or a propellant.

Preferably, the medicament consists of particles of activated carbon having an average particle size greater than 0.05 mm. For example, if the particle size is determined by sieving a portion of powder through a graded series of sieves, the average particles size determined in this way is preferably greater than 0.05 mm. If the average particle size is lower than 0.05 mm then the medicament may be difficult to handle, as it will be prone to forming an airborne dust. Such fine particles are difficult to wet and may also clump or agglomerate during storage and, therefore, may not flush from the cannula easily. The applicant's experiments indicate that if fine particles having average particle size lower than 0.05 mm are used, 20% to 50% of the particles (i.e. the dose) may be retained in the syringe and therefore not actually administered.

The applicants have found that if the activated carbon is of particle size 0.15 mm to 1 mm, it is preferred that the fluid (driving fluid) is a liquid (e.g. water). The applicants have surprisingly found that if the activated carbon is of particle size 0.05 mm to 0.15 mm, the fluid (driving fluid) may be a liquid (e.g. water) or a gas (e.g. air).

In addition to the preferred particle size ranges stated above, it is preferred that the activated carbon has a bulk density or apparent density of from 0.015 to 0.6 g/cm$^3$, for example from 0.4 g/cm$^3$ to 0.5 g/cm$^3$, preferably from 0.44 g/cm$^3$ to 0.45 g/cm$^3$. Bulk density may be calculated according to the standard procedure set out in ASTM D2854. The bulk density may be from 0.15 to 0.05 g/cm$^3$.

The activated carbon particles are formed by grinding carbon material to the desired size.

Loading the cannula with the pharmaceutical composition may be an action undertaken by a patient. However, it may be convenient if the device is preloaded with the pharmaceutical composition. The pharmaceutical composition may, therefore, be loaded into the cannula cavity under controlled conditions and sealed at one end by the openable closure and at the other end by a sealing means. Such sealing means may, for example, be a removable seal that is removed by the user before delivery or a frangible seal that breaks on actuation. A suitable sealing means may be a cap or sheath that protects the external surface of the cannula, or at least of an insertable portion of the cannula. The sealing means may even be a second one-way valve that allows passage of the contents of the cavity to pass out of the cannula when the device is actuated.

The actuation means may be a manually-operated actuator for example a syringe or a bellows or a bulb. The manually-operated actuator is preferably capable of being filled with a driving liquid from a source of such liquid. For example, if the driving liquid is water then the water may be supplied as sterile water for injection in a container, such as a flask or a vial, and then transferred to an actuation means, such as a syringe, prior to use of the device. It is preferable, therefore, that the actuation means is removably coupleable from the device to allow it to be filled or loaded with the driving liquid and then coupled to the device in a suitable arrangement for forcing the driving liquid through the one-way valve into the cannula cavity. It may be advantageous for the actuation means to be an automatic actuator that delivers a volume of a driving liquid on, for example, the press of a button. For example the actuation means may be a motorised actuator that is operable to drive liquid from a source of liquid through the one-way valve and the cannula cavity to deliver the dose of particular pharmaceutical composition.

The device may comprise a flange or collar that extends radially outwards from an external surface of the cannula at a predetermined distance from the distal opening to determine the maximum depth of insertion of the cannula into the patient's rectum. Such a flange or collar presents a physical barrier that prevents or hinders a portion of the cannula proximal to the flange or collar from easily being inserted through a patient's anus. The flange or collar may also help provide a user with purchase on the cannula to allow the application of insertion force in the direction of a longitudinal axis of the cannula. For example, a user may apply a force on a proximal surface of a flange or collar in order to insert the cannula to a depth at which a distal surface of the flange or collar abuts the patient's anus.

The cannula may be preloaded with pharmaceutical composition in a controlled environment. In such circumstances the loaded cannula may be conveniently supplied as a disposable component containing a preloaded volume of pharmaceutical composition. Such a preloaded cannula could be attached to a device, the device could be activated to deliver the pharmaceutical composition, and then the spent cannula could be removed from the device and disposed of.

It may be convenient for a patient suffering from pouchitis or proctitis to be supplied with a kit of parts for treatment of the disease comprising a device as described above. Thus, a further aspect of the invention may provide a kit for the treatment of pouchitis or proctitis comprising a delivery device (e.g. as described above); a supply of activated carbon particles of particle size 0.001 to 1 mm, for example 0.02 to 1 mm, preferably 0.05 to 1 mm (for example 0.1 to 0.5 mm, for example 0.5 mm to 0.4 mm, for example 0.15 to 0.3 mm, for example 0.2 to 0.3 mm); and optionally a source of fluid (e.g. liquid) for flushing the activated carbon particles through the device. The activated carbon may be of particle size 0.15 to 1 mm. The delivery device is preferably a device for rectal delivery of activated carbon.

Preferably the activated carbon is of average particle size 0.15 to 0.3 mm. A still further aspect of the invention may provide a kit for the treatment of pouchitis or proctitis comprising a delivery device (e.g. as described above); a supply of activated carbon particles wherein 85% or more of the activated carbon particles have diameter in the range from 0.089 mm to 0.3 mm (e.g. wherein 85% or more of the activated carbon particles have diameter in the range from 0.152 mm to 0.297 mm); and optionally a source of fluid (e.g. liquid) for flushing the activated carbon particles through the device.

The fluid for flushing the activated carbon particles could be any suitable liquid. Preferably the liquid is a liquid that does not influence the adsorptive properties of the activated carbon particles and is safe for injection into a patient's rectum. The skilled person will be aware of many such suitable liquids but as an example the liquid may be sterile water, for example water for injection, a salt solution, etc. The fluid may be a gas (e.g. air).

As described above, it may be advantageous for the activated carbon particles to be preloaded into disposable, rectally-insertable, cannulas. Thus, the invention may further provide a kit for the treatment of pouchitis or proctitis comprising a disposable, rectally-insertable, cannula including (e.g. a single dose of) activated carbon particles of particle size 0.001 to 1 mm, for example 0.02 to 1 mm, preferably 0.05 to 1 mm [for example 0.1 to 0.5 mm, for example 0.5 mm to 0.4 mm, for example 0.2 to 0.3 mm]; and optionally an activation means that can be filled or loaded with a volume of driving fluid (e.g. liquid). The activated carbon may be of particle size 0.15 to 1 mm. Preferably the activated carbon is of average particle size 0.15 to 0.3 mm.

The invention may further provide a kit for the treatment of pouchitis or proctitis comprising a disposable, rectally-insertable, cannula including (e.g. a single dose of) activated carbon particles wherein 85% or more of the activated carbon particles have diameter in the range from 0.089 mm to 0.3 mm (e.g. wherein 85% or more of the activated carbon particles have diameter in the range from 0.152 mm to 0.297 mm); and optionally an activation means that can be filled or loaded with a volume of driving fluid (e.g. liquid or gas such as air).

The disposable cannula may be removably-coupleable to the activation means such that the activation means is capable of driving a volume of the fluid (e.g. liquid) through the openable closure of the cannula and the cannula cavity to flush the dose of activated carbon out of the cannula cavity through the distal opening of the cannula. The kit may also comprise a supply of the driving liquid/fluid. Preferably, the kit comprises a plurality of rectally-insertable cannulas, each cannula being removably-coupleable to the activation means and each cannula being loaded with a single dose of activated carbon. Preferably the activated carbon is of average particle size 0.15 to 0.3 mm.

The applicants have also developed a formulation comprising activated carbon for (use in) the treatment of a condition or disorder related to mucosal barrier dysfunction in the gut (gastrointestinal tract), for oral administration which retains, to a high degree, the adsorbtive (pharmaceutical) activity of activated carbon following oral administration until it reaches the site of action, and/or which minimises adsorbtion of essential chemicals and nutrients by the activated carbon while passing through the patient's stomach etc. to the site of action.

Thus, the composition (e.g. pharmaceutical composition) (for oral use) may comprise:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH 7, e.g. a layer which breaks down rapidly (dissolves) at pH 5, a layer which breaks down rapidly (dissolves) at pH≥5.5, a layer which dissolves at pH 7 etc.) and/or which dissolves at a predetermined location in the gastrointestinal tract.

The composition for oral administration may be in the form of a powder, suspension, tablet, capsule etc.

The composition may be for treatment of a condition or disorder related to mucosal barrier dysfunction in the gut (gastrointestinal tract). The condition or disorder related to mucosal barrier dysfunction in the gut may be caused by translocation (i.e. caused by leaking in the gastrointestinal mucosa such that substances that should be remain in the lumen of the gut pass across the gut epithelium into the body). The condition or disorder related to mucosal barrier dysfunction in the gut may be proctitis (including radiation proctitis), pouchitis, ulcerative colitis, Crohns disease, IBS, ascites (associated with liver cirrhosis), pancreatitis or radiation enteritis.

The following discusses the components of the new compositions described herein in more detail.

(b) the First Layer Around the Core, the First Layer Comprising an Insoluble Semipermeable Material:

The first (e.g. an inner) layer may comprise an insoluble semipermeable membrane.

Herein, the term "semipermeable" means that the material (layer) allows (e.g. gradual) diffusion of molecules and ions through the semipermeable material (layer) towards the core and into contact with the activated carbon and/or allows (e.g. gradual) diffusion of selected molecules and ions through the semipermeable material (layer) towards the core and into contact with the activated carbon. The (e.g. selected) molecules and ions may be materials (e.g. toxins or local irritants) which provoke irritation in the gut (e.g. colon and/or rectum). The (e.g. selected) molecules/ions may be molecules/ions which are produced by the body. The first (e.g. an inner) layer may comprise a material (a semipermeable membrane) which allows (e.g. gradual) diffusion of molecules and ions through the semipermeable material (layer) towards the core and into contact with the activated carbon. Preferably, the (insoluble semipermeable) material does not substantially inactivate the activated carbon.

It will be appreciated that the material of the first layer may be selected based on the molecules and/or ions (e.g. substances which cause, maintain, promote or exacerbate mucosal barrier dysfunction in the gut, e.g. proctitis and/or pouchitis) which are to be adsorbed by the activated carbon (and hence removed by excretion).

The first (e.g. inner) layer comprises an insoluble semipermeable material (e.g. a semipermeable membrane). In examples, the insoluble semipermeable material may be, for example, ethyl cellulose; a poly(meth)acrylate polymer such as EUDRAGIT® RL 100, EUDRAGIT® RL PO, EUDRAGIT® RL 30D, EUDRAGIT® RL 12.5, EUDRAGIT® RS 100, EUDRAGIT® RS PO, EUDRAGIT® RS 30D, EUDRAGIT® RS 12.5, EUDRAGIT® NE 30D, EUDRAGIT® NE 40D, all available from Evonik, glycerylmonostearate, cellulose acetate butyrate, dipolylactic acid, polyvinyl chloride. The first (e.g. inner) layer may further comprise a water soluble material (e.g. a water soluble polymer). The water soluble material (e.g. water soluble polymer) may be mixed with the insoluble semipermeable material (e.g. dispersed within the semipermerable material/membrane). In examples, the water soluble material may be, for example sugar, PVA, PVP, hydroxypropylmethyl cellulose (HPMC), carboxymethylcellulose, sodium carboxymethyl cellulose, salts, sugar alcohols etc. The water soluble material (e.g. water soluble polymer, e.g. HPMC) may be included in an amount which is 0.1 to 30% by weight of the amount of the insoluble semipermeable material (e.g. ethylcellulose) in the layer (b), for example in an amount which is 2 to 25% by weight of the amount of the insoluble semipermeable material (e.g. ethylcellulose) in the layer (b), for example 5 to 15% by weight of the amount of the insoluble semipermeable material in the layer, for example 10% by weight of the amount of the insoluble semipermeable material in the layer.

The water soluble material (e.g. water soluble polymer, e.g. HPMC) may increase the permeability of the insoluble semipermeable material (e.g. ethyl cellulose). For example, dissolution of the water soluble material e.g. HPMC may form defects or channels in the ethyl cellulose coating, when the first layer is exposed after removal of the second (e.g. enteric) layer (see below), to thereby enable the adsorptive capacity of the activated carbon within the layer. Without being bound by theory, it is believed that the channels allow diffusion of material (e.g. substances which cause, maintain, promote or exacerbate mucosal barrier dysfunction in the gut, e.g. proctitis and/or pouchitis) across the first layer, so it may be adsorbed on the activated carbon. The rate of diffusion may therefore be controlled by the amount of water soluble material (e.g. water soluble polymer, e.g. HPMC), and also the thickness of the film; if the film is thinner, there will be a faster diffusion.

The thickness of the first layer around the core may correspond to a theoretical weight increase (of the core) from the layer (film coating) of 1 to 20%, for example 2 to 10%, for example 3 to 7%, for example 4%. It has been found that a coating of around this thickness provides an effective adsorption capacity.

The first (e.g. inner) layer may consist essentially of the insoluble semipermeable material (e.g. ethyl cellulose) and the water soluble material (e.g. water soluble polymer, e.g. HPMC). Avoiding the use of some other ingredients/excipients in the layer (b) prevents loss of adsorptive capacity of the activated carbon to these excipients.

The insoluble semipermeable material may be an insoluble membrane which includes pores, for example a mixture of ethylcellulose with high- or low viscosity HPMC (hydroxypropyl methylcellulose).

The first (e.g. an inner) layer may comprise a mixture of ethylcellulose with high- or low viscosity HPMC (hydroxypropyl methylcellulose).

The first (e.g. an inner) layer may comprise a mixture of copolymers composed of 85 to 98% by weight free-radical polymerized $C_1$- to $C_4$-alkyl esters of acrylic or methacrylic acid and 15 to 2% by weight (methy) acrylate monomers with a quaternary ammonium group in the alkyl radical. $C_1$- to $C_4$-alkyl esters of acrylic or methacrylic acid are methyl methacrylate, butyl methacrylate, methyl acrylate, ethyl acrylate, butyl acrylate. A preferred (methy) acrylate monomer with a quaternary ammonium group is 2-trimethylammoniummethyl methacrylate chloride.

In other examples, the first (e.g. an inner) layer may comprise a mixture of copolymers composed of 85 to 98% by weight free-radical polymerized $C_1$- to $C_4$-alkyl esters of acrylic or methacrylic acid and 15 to 2% by weight (methy) acrylate monomers with a quaternary ammonium group in the alkyl radical. $C_1$- to $C_4$-alkyl esters of acrylic or methacrylic acid are methyl methacrylate, butyl methacrylate, methyl acrylate, ethyl acrylate, butyl acrylate. A preferred (methy) acrylate monomer with a quaternary ammonium group is 2-trimethylammoniummethyl methacrylate chloride.

The first layer may be a copolymer comprising 65% by weight methyl methacrylate, 30% by weight ethyl acrylate and 5% by weight 2-trimethylammoniummethyl methacrylate chloride. Such copolymers are commercially available and known as EUDRAGIT® RS type polymers, for example EUDRAGIT® RS 100, EUDRAGIT® RS PO, EUDRAGIT® RS 30D, EUDRAGIT® RS 12.5 etc., available from Evonik Industries. Preferably, the first layer comprises EUDRAGIT® RS 30 D, available from Evonik Industries.

The first (e.g. an inner) layer may comprise a mixture of copolymers composed of 85 to less than 93% by weight free-radical polymerized $C_1$- to $C_4$-alkyl esters of acrylic or methacrylic acid and 15 to more than 7% by weight 2-trimethylammoniummethyl methacrylate chloride. The first (e.g. an inner) layer may comprise 50 to 70% by weight methyl methacrylate, and 20 to 40% by weight ethyl acrylate.

The first layer may be a copolymer comprising 60% by weight methyl methacrylate, 30% by weight ethyl acrylate and 10% by weight 2-trimethylammoniummethyl methacrylate chloride. Such copolymers are commercially available and known as EUDRAGIT® RL type polymers, for example EUDRAGIT® RL 100, EUDRAGIT® RL PO, EUDRAGIT® RL 30D, EUDRAGIT® RL 12.5 etc., available from Evonik Industries. Preferably, the first layer comprises EUDRAGIT® RL 30 D, available from Evonik Industries.

Preferably, the first (e.g. inner) layer comprises a mixture of a first copolymer comprising 65% by weight methyl methacrylate, 30% by weight ethyl acrylate and 5% by weight 2-trimethylammoniummethyl methacrylate chloride (EUDRAGIT® RS) and a second copolymer comprising 60% by weight methyl methacrylate, 30% by weight ethyl acrylate and 10% by weight 2-trimethylammoniummethyl methacrylate chloride (EUDRAGIT® RL).

The first layer may be EUDRAGIT® NE 30D or EUDRAGIT® NE 40D, available from Evonik.

The amount of the first (e.g. an inner) layer may be 2 to 20% by weight based on the weight of the core with the activated carbon.

(c) the Second Layer Around the First Layer which Dissolves at a Predetermined PH and/or which Dissolves at a Predetermined Location in the Gastrointestinal Tract:

The second (e.g. outer) layer prevents or reduces exposure of the first layer (and the activated carbon) to the digestive system environment, until a predetermined point in the digestive system after the stomach. The second (e.g. outer) layer may, for example, prevent or reduce exposure of the first layer (and the activated carbon) to the digestive system environment, until the composition reaches the lower part of the intestine, i.e. the late ileum, caecum and/or colon. The second layer may be selected from coatings which are pH-sensitive, redox-sensitive or sensitive to particular enzymes or bacteria. It will be appreciated that the mechanism of action of the compositions of the present invention (which holds the activated carbon within the inner membrane/layer) is completely opposite to controlled release formulations where an enteric coating is used to protect an inner layer (as it travels through the stomach) but then dissolves in the intestine to expose the inner layer which immediately releases the active pharmaceutical in the lower digestive tract.

The second layer may be a material which remains substantially intact (e.g. is highly stable, e.g. does not disintegrate or dissolve) at (e.g. highly) acidic pH found in the stomach (e.g. pH 1 to 3), but which breaks down rapidly (dissolves) at less acidic (more basic) pH, for example at pH 5 to 7, e.g. pH 5.5. Preferably the second (e.g. outer) layer is a pH sensitive polymer. The second (e.g. outer) layer may be a polymer which breaks down rapidly (dissolves) at a pH of about 5. The second (e.g. outer) layer may be a polymer which breaks down rapidly (dissolves) at a pH of about 7. The amount of second (e.g. outer) layer (e.g. the enteric layer) may be 2 to 35% or even up to 50% w/w of the total composition, for example the amount of second (e.g. outer) layer (e.g. the enteric layer) may be 8 to 16% w/w of the total composition, for example 10 to 14% w/w of the total composition, for example 12% w/w of the total composition.

The thickness of the second (e.g. outer) layer (e.g. the enteric layer) around the core may correspond to a theoretical weight increase (of the core and first layer) from the film coating of 4 to 16%, for example 6% to 14%, for example 8% or 12%. It was found that such a coating should ensure passage of the stomach prior to exposure of the first layer.

Preferably the second (e.g. outer layer) is an enteric layer. The enteric layer (enteric coating layer) prevents or reduces exposure of the first layer (and the activated carbon) to the digestive system environment, until the composition reaches the small intestine (and even after the composition reaches the small intestine the semipermeable membrane may minimise or prevent adsorption of beneficial substances such as nutrients by the activated carbon).

In some preferred examples, the layer(s) are chosen so the first (inner) layer is exposed in the small intestine, preferably close to the colon (to minimise adsorption of beneficial substances and reserve the bulk of the adsorptive capacity until the colon is reached). Preferably, the enteric layer is a material which remains substantially intact (is highly stable) at (e.g. highly) acidic pH found in the stomach (e.g. pH 1 to 3) but which breaks down rapidly (dissolves) at less acidic (more basic) pH, for example at pH 5 to 7, e.g. pH≥5.5, for example pH 7 as found in small intestine. Preferably the enteric layer (enteric coating layer) is a pH sensitive polymer. The pH sensitive polymer may have a free acid group (carboxylic acid group) with dissolution caused by deprotonation of the acid group. The enteric layer (enteric coating layer) may be a polymer which breaks down rapidly (dissolves) at a pH of about 5. The enteric layer (enteric coating layer) may be a polymer which breaks down rapidly (dissolves) at a pH of about 7. The enteric layer (enteric coating layer) may be a water soluble polymer. The enteric layer may comprise one or more of a methyl acrylate-methacrylic acid copolymer, cellulose acetate succinate, hydroxy propyl methyl cellulose phthalate, hydroxyl propyl methyl cellulose acetate succinate, polyvinyl acetate phthalate (PVAP), methyl methacrylate-methacrylic acid copolymer, sodium alginate and stearic acid. The enteric layer may be a fatty acid, wax, shellac, plastics material etc. The enteric layer may be a pH-dependent enterosoluble polymers, such as cellulose acetate trimellitate (CAT), cellulose acetate phthalate (CAP), anionic copolymers based on methylacrylate, methylmethacrylate and methacrylic acid, hydroxypropyl methylcellulose phthalate (HPMCP), hydroxypropylmethylcellulose acetate succinate (HPMCAS), methacrylic acid and ethyl acrylate copolymers, methacrylic acid and ethyl acrylate copolymers, methacrylic acid and methyl methacrylate copolymers (1:1 ratio), methacrylic acid and methyl methacrylate copolymers (1:2 ratio), Polyvinyl acetate phthalate (PVAP) and Shellac resins. The enteric layer may be EUDRAGIT® E100, E12.5 or E PO. The enteric layer may be, for example, EUDRAGIT® L 100, EUDRAGIT® L 30D, a mixture of EUDRAGIT® S 100/FS 30 D and EUDRAGIT® L 100 (see below). These EUDRAGIT® products are available from Evonik Industries.

The enteric layer may comprise hydroxypropylmethylcellulose acetate succinate (HPMC AS), for example a HMPC AS which dissolves at pH between 5.5 to 6.8. As is known in the art, it is possible to vary the content of acetate and succinate in HPMC AS to provide an enteric coating which dissolves from pH>5.5 to pH>6.8. The enteric layer may consist of, or consist essentially of, hydroxypropylmethylcellulose acetate succinate (HPMC AS), for example a HMPC AS which dissolves at pH between 5.5 to 6.8.

The amount of enteric layer may be 2 to 35% or even up to 50% w/w of the total composition, for example the amount of the enteric layer may be 8 to 16% w/w of the total composition, for example 10 to 14% w/w of the total composition, for example 12% w/w of the total composition.

The thickness of the second (e.g. outer) layer (e.g. the enteric layer) around the core may correspond to a theoretical weight increase (of the core and first layer) from the film coating of 4 to 16%, for example 6% to 14%, for example 8% or 12%. It was found from tests that such a coating should ensure passage of the stomach prior to exposure of the first layer.

The enteric layer (enteric coating layer) may comprise a copolymer composed of 80 to 95% by weight free-radical polymerized $C_1$- to $C_4$-alkyl esters of acrylic or methacrylic acid and 5 to 25% by weight (meth)acrylate monomers with an anionic group in the alkyl radical. $C_1$- to $C_4$-alkyl esters of acrylic or methacrylic acid are methyl methacrylate, ethyl methacrylate, butyl methacrylate, methyl acrylate, ethyl acrylate, butyl acrylate.

A (meth)acrylate monomer with an anionic group in the alkyl radical may be, for example, acrylic acid or methacrylic acid.

The enteric layer may be a (meth)acrylate copolymer comprising 10 to 30% by weight methyl methacrylate, 50 to 70% by weight methyl acrylate and 5 to 15% by weight methacrylic acid. Such polymers are commercially available and known as EUDRAGIT® FS type polymers. Preferably, the enteric layer comprises EUDRAGIT® FS 30 D, available from Evonik Industries.

The enteric layer may be EUDRAGIT® E100, E12.5 or E PO. The enteric layer may be, for example, EUDRAGIT® L 100, EUDRAGIT® L 30D, a mixture of EUDRAGIT® S 100/FS 30 D and EUDRAGIT® L 100 (see below). These EUDRAGIT® products are available from Evonik Industries.

The amount of the second (enteric) layer may be 5 to 15% by weight based on the weight of the core with the activated carbon and the inner layer.

While not being limited by any theory, it will be appreciated that examples of the invention may work as follows. The outer (e.g. enteric) layer of the composition remains substantially intact at the acidic pH found in the stomach (e.g. pH 1 to 3), and the pharmaceutical composition therefore remains substantially intact as it travels to and through the stomach following oral administration. However, the outer (e.g. enteric) layer breaks down and dissolves at the pH found in the small intestine (e.g. pH 5 found in the upper part of the small intestine, or pH 7 found in the lower part of the small intestine), thereby exposing the first (e.g. inner) layer. It should be noted that even after the composition reaches the small intestine (and the enteric layer dissolves) the semipermeable membrane (in the first layer) may minimise adsorption of beneficial substances such as nutrients by the activated carbon. In some preferred examples, the layer(s) are chosen so the first (inner) layer is exposed in the lower part of the small intestine, preferably close to the colon (to minimise adsorption of beneficial substances and save the bulk of the adsorptive capacity for the colon). The first layer comprises a material (e.g. a semipermeable membrane) which may allow gradual diffusion of molecules and ions (e.g. substances which cause, maintain, promote or exacerbate mucosal barrier dysfunction in the gut, e.g. proctitis and/or pouchitis) through the semipermeable membrane towards the core into contact with the activated carbon, where they are adsorbed. In some examples, dissolution of a water soluble material (e.g. HPMC) in the semipermeable material (e.g. ethyl cellulose) may form defects or channels in the semiperpeable material/layer, when the first (e.g. inner) layer is exposed after removal of the second (e.g. enteric) layer, to thereby slowly enable the adsorptive capacity of the activated carbon within the layer. The (insoluble semipermeable) material does not substantially inactivate the activated carbon, so the activated carbon is available to adsorb these molecules/ions. It will be appreciated that substantially all of the activated carbon is held (remains) within the semipermeable membrane as the composition (minus the outer layer) travels on through the digestive system (e.g. through the lower part of the small intestine and the colon); the activated carbon is not released and is therefore less able to remove (adsorb) essential chemicals such as nutrients.

It will be appreciated that inclusion of the semipermeable membrane (the first, inner, layer) may enable the adsorptive capacity of the activated carbon to be maintained as the composition travels through the whole large intestine [and the formulations may even retain some adsorptive capacity even as they pass through the rectum and anus (i.e. the compositions of the invention may still have adsorptive capacity while they are in the rectum or anus)]. If the semipermeable membrane/first layer were not present the removal of the outer (enteric) layer would make all of the adsorptive capacity of the activated carbon available at once (e.g. at the top of the small intestine), and the amount of adsorptive activity remaining available by the time the composition reached the large intestine may be insufficient to treat the medical condition.

Without wishing to be bound by theory, it is believed that molecules (e.g. substances which cause, maintain, promote or exacerbate mucosal barrier dysfunction in the gut, e.g. proctitis and/or pouchitis) are able to diffuse through the semipermeable membrane where they are adsorbed by the activated carbon and then held on the carbon and subsequently removed by excretion. It will be appreciated that the mechanism of action of the compositions of the present invention (which holds the activated carbon within the inner membrane/layer) is completely opposite to controlled release formulations where an enteric coating is used to protect an inner layer (as it travels through the stomach) but then dissolves in the intestine to expose the inner layer which immediately releases the active pharmaceutical in the lower digestive tract.

The applicants have found that the compositions of the invention may provide a more constant adsorption as they proceed through the gut (after removal of the enteric layer). The retention of adsorptive capacity of activated carbon through the gut (even, depending on the coating used, until the rectum or anus) is important because the exact location of the mucosal barrier dysfunction in the gut may not be known.

(a) A Core Comprising Activated Carbon

The core comprises activated carbon. Preferably the core consists of, or consists essentially of, activated carbon. In other words, it is preferred that the core is 100% activated carbon (i.e. activated carbon alone, without other excipients or active ingredients). Thus, preferably the core does not include carrageenan (or a granulation enhancer etc.). The applicants have surprisingly found that it is possible to work with and coat individual granules of activated carbon (e.g. of specific size and/or hardness) without requirement for a granulation excipients such as carrageenan.

The activated carbon is preferably sanded or deburred. Herein, the term "deburred" means untreated "raw" activated carbon is subjected to a finishing process to reduce or minimise the number of tips, peaks and edges (from the surface). The activated carbon may be deburred by the process described below. The active carbon may be deburred or sanded by causing the untreated activated carbon particles to collide with each other at high speed (e.g. speeds from 30 to 300 km/h, for example 35 to 70 km/h). The burred or sanded activated carbon (of specific size) may then be separated for use in/as core (a).

The activated carbon may include 0.9 or fewer tips peaks and edges of height 20-100 µm per particle or granule, for example 0.8 tips or fewer peaks and edges per particle/granule, for example 0.6 tips peaks and edges or fewer per particle/granule.

The activated carbon may be, for example, of particle size 0.02 to 5 mm (depending on the raw material from which the activated carbon is made). The activated carbon may be, for example, of particle size 0.02 to 2.1 mm, for example 0.05 to 2.1 mm, for example 0.1 to 2 mm, for example 0.2 to 2 mm. The activated carbon may be of particle size from 0.6 to 1.2 mm. The activated carbon of this particle size may be selected by sieving the activated carbon (e.g. after it has been sanded/deburred); by selecting activated carbon which includes particles that will pass through a 1.2 mm sieve (i.e. a sieve having aperture size 1.2 mm) but will not pass through a 0.6 mm sieve. Preferably the activated carbon is of particle size from 0.6 to 1.0 mm. The activated carbon of this particle size may be selected by sieving activated carbon (e.g. after it has been sanded/deburred); the preferred activated carbon includes particles that will pass through a 1.0 mm sieve (i.e. a sieve having aperture size 1.0 mm) but will not pass through a 0.6 mm sieve. Herein the term "particle size" means the width at the narrowest point of the activated carbon particle or granule (e.g the diameter for a spherical or roughly spherical particle).

The activated carbon may be made from coconut shells.

Activated carbon (e.g. granular activated carbon) and its methods of manufacture is well known in the art and is available from, for example, Chemviron Carbon.

The applicants have found that activated carbon of particle size between 0.6 to 1.2 mm (e.g. 0.6 to 1.0 mm) and/or which has been sanded or deburred is ready to process (i.e. coat with the first layer); there is no need to granulate/process/extrude/spheronise the carbon or add a granulating agent such as carrageenan. This simplifies the process and means that each core has very high absorption capacity (the core is all activated carbon and there are no excipients etc. present to "dilute" the adsorption capacity). Further, the deburring has the effect of stabilising the adsorbtion rate. Sanding or deburring the raw activated carbon reduces the number of edges (per gram) on the surface of the activated carbon. The raw material is itself very hard to coat consistently, due to the roughness. If the particle is rough, there is high variation in coating thickness over the surface of the overall particle, which has an effect on coating homogeneity and resulting exposure of adsorptive capacity prematurely (e.g. before the colon). Smoothing the activated carbon by sanding or deburring the surface means that the coating thickness is more consistent: the adsorptive capacity of activated carbon is provided in the appropriate place (e.g. in the colon)

The activated carbon may be granular activated carbon. Preferably the core is a granule of activated carbon. It is preferred that the activated carbon particles/granules are formed by grinding or milling carbon material to the desired size. Ground activated carbon has an irregular particle shape. The activated carbon may be in the form of spheronised or spherical particles. The activated carbon may be coated. The activated carbon may be a pharmaceutical or medical grade activated carbon (e.g. activated carbon which complies with Ph. Eur., apart from the particle size).

Preferably the activated carbon is made from coconut shells.

It is preferred that the activated carbon is the sole active pharmaceutical ingredient. Further, it is preferred that the core does not include carrageenan.

According to the present invention in a further aspect there is provides a composition for use in the treatment of a condition or disorder related to mucosal barrier dysfunction in the gut (gastrointestinal tract), the composition being for oral administration and comprising:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH 7, e.g. a layer which breaks down rapidly (dissolves) at pH 5, a layer which breaks down rapidly (dissolves) at pH≥5.5, a layer which dissolves at pH 7 etc.) and/or which dissolves at a predetermined location in the gastrointestinal tract. The components (a), (b) and (c) may be as described herein.

The insoluble semipermeable material may be an insoluble membrane which includes pores, for example a mixture of ethylcellulose with high- or low viscosity HPMC (hydroxypropyl methylcellulose).

The first (e.g. an inner) layer may comprise a mixture of ethylcellulose with high- or low viscosity HPMC (hydroxypropyl methylcellulose).

The condition or disorder related to mucosal barrier dysfunction in the gut may be caused by translocation (i.e. caused by leaking in the gastrointestinal mucosa such that substances that should be remain in the lumen of the gut pass across the gut epithelium into the body). The condition or disorder related to mucosal barrier dysfunction in the gut may be proctitis (including radiation proctitis), pouchitis, ulcerative colitis. Crohns disease, IBS, ascites (associated with liver cirrhosis), pancreatitis or radiation enteritis.

The composition for oral administration may be in the form of a powder, suspension, tablet, capsule etc.

According to the present invention in a further aspect there is provides a method of treatment of a condition or disorder related to mucosal barrier dysfunction in the gut (gastrointestinal tract), the composition being comprising a step of orally administering (to a subject in need thereof) an oral pharmaceutical composition comprising:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH 7, e.g. a layer which breaks down rapidly (dissolves) at pH 5, a layer which breaks down rapidly (dissolves) at pH≥5.5, a layer which dissolves at pH 7 etc.) and/or which dissolves at a predetermined location in the gastrointestinal tract. The components (a), (b) and (c) may be as described herein. The insoluble semipermeable material may be an insoluble membrane which includes pores, for example a mixture of ethylcellulose with high- or low viscosity HPMC (hydroxypropyl methylcellulose).

The first (e.g. an inner) layer may comprise a mixture of ethylcellulose with high- or low viscosity HPMC (hydroxypropyl methylcellulose).

The condition or disorder related to mucosal barrier dysfunction in the gut may be caused by translocation (i.e. caused by leaking in the gastrointestinal mucosa such that substances that should be remain in the lumen of the gut pass across the gut epithelium into the body). The condition or disorder related to mucosal barrier dysfunction in the gut may be proctitis (including radiation proctitis), pouchitis, ulcerative colitis, Crohns disease, IBS, ascites (associated with liver cirrhosis), pancreatitis or radiation enteritis.

The orally administrable composition may be administered as a powder, suspension, tablet, capsule etc.

SPECIFIC EMBODIMENTS OF THE INVENTION

Specific embodiments of the invention will now be described with reference to the Figures in which:

FIG. 1 illustrates a device for delivering a dose of a pharmaceutical composition for use in the treatment of pouchitis or proctitis according to an embodiment of the invention comprising activated carbon particles;

FIG. 2 illustrates a rectally-insertable cannula for use as a component part of the device illustrated in FIG. 1;

FIG. 1 illustrates a device 10 for delivering a dose of a pharmaceutical composition comprising activated carbon particles into a patient's rectal cavity. The patient has been diagnosed with proctitis (or pouchitis) by a medical professional (e.g. doctor) and has been assessed as being suitable for, and likely to be responsive to, such treatment. The device comprises a rectally-insertable cannula 20, a syringe 30, and a length of flexible tubing 40 coupling the syringe 30 to the cannula 20.

Figure 3:
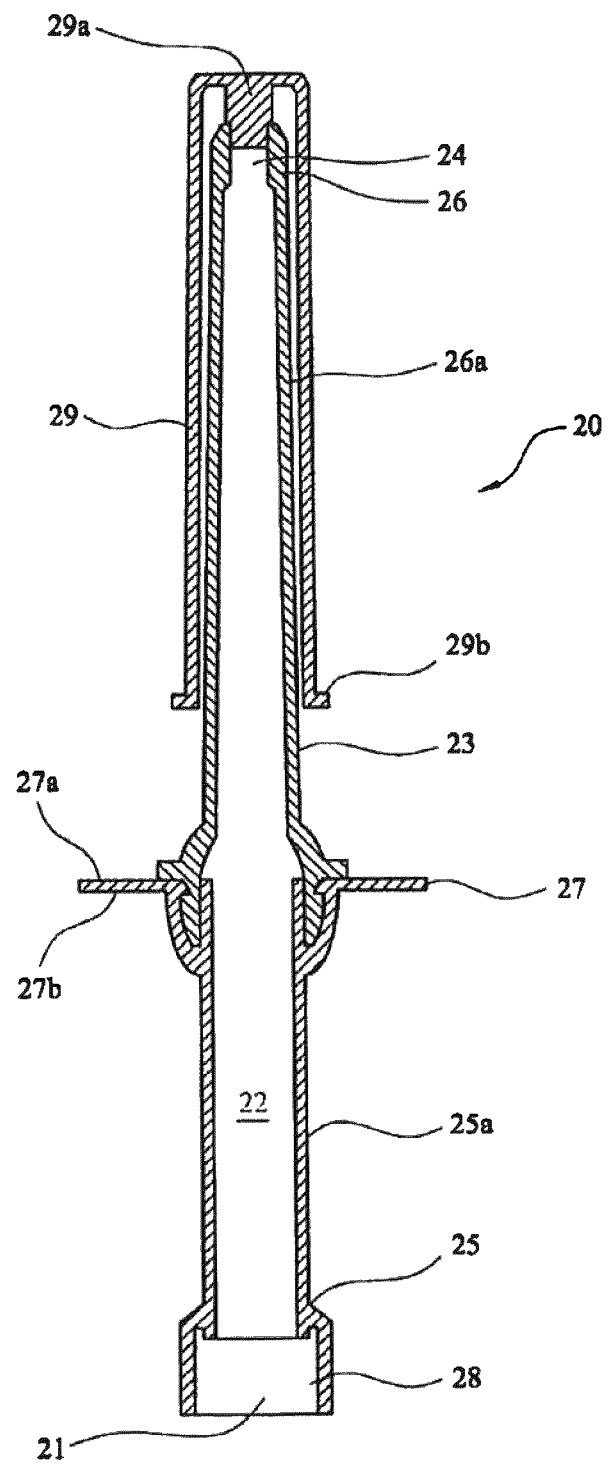
FIG. 3 illustrates a longitudinal cross-section of the rectally-insertable cannula of FIG. 2.

The cannula 20 is illustrated in greater detail in FIGS. 2 and 3. The cannula 20 has a generally elongated shape and has a proximal end 25 and a distal end 26. A cavity 22 is defined within a body 23 of the cannula 20, the cavity having a proximal opening 21 at the proximal end of the cannula leading into the cavity 22 and a distal opening 24 at the distal end of the cannula leading out of the cavity 22. The cavity 22 extends longitudinally between the proximal opening 21 and the distal opening 24.

The body 23 of the cannula 20 further defines a radially-extending flange or collar 27, which extends around a circumference of the cannula body 23 between the proximal end 25 and the distal end 26. A portion of the cannula body extending from the radially-extending flange toward the proximal end of the cannula may be termed a proximal portion 25a of the cannula body 23. Likewise, a portion of the cannula body 23 extending from the radially-extending flange 27 to the distal end 26 may be termed a distal portion 26a of the cannula.

In the specific embodiment described herein, the cannula is formed as a two-piece construction. Thus, the distal portion of the cannula body 26a and the proximal portion of the cannula body 25a are formed as separate polyethylene components and then joined together to form the cannula 20. The radially-extending flange is formed as part of the proximal portion of the cannula 25a, but could clearly be formed as part of the distal portion of the cannula 26a. The cannula may also be formed as a single component.

The distal portion 26a of the cannula is externally-sized and shaped to be inserted through a human anus into a human rectum in order to deliver the pharmaceutical composition into the patient's rectal ampulla. Accordingly, the distal portion 26a has a length of 7 cm and has a substantially circular external cross-section. The distal portion 26a is tapered at an angle of about 2° and has an outer diameter of 6.5 mm at the distal end 26. The radially-extending flange 27 has a substantially circular cross-section and a diameter of 3.0 cm. The proximal portion 25a of the cannula body 23 is also of substantially circular cross-section and tapers from an inner diameter of about 7.7 mm (outer diameter 15.5 mm) adjacent to the radially-extending flange to an inner diameter of about 6.3 mm (outer diameter 8.7 mm) at the proximal end 25 of the cannula.

The cavity 22 defined within the cannula body 23 extends longitudinally through the cannula body from the proximal end 25 to the distal end 26. At the distal end 26 the cavity terminates at the distal opening 24. The distal opening is of substantially circular cross-section and has a diameter of 2.8 mm. At the proximal end of the cannula the cavity 22 is spanned by a one-way valve (not shown). The diameter of the cannula at the proximal end is 6.3 mm. The one-way valve 50 is actuatable to allow fluids (e.g. liquids) to enter the cavity 22 through the proximal opening 21 of the cannula, but does not allow the passage of material contained within the cavity 22 of the cannula out of the cavity through the proximal opening 21. The cavity is about 120 mm in total length from the proximal opening to the distal opening. The cavity has a maximum diameter in the region of the radially-extending flange, where the internal cavity diameter is 7.7 mm. The volume of the cavity is about 2.6 cm³, and the cannula is designed to be loaded with about 1.2 gram or about 1.3 gram of activated carbon particles having a bulk density of about 0.45 g/cm³.

An upper surface 27a of the radially-extending flange 27 acts as a stop to prevent the cannula from being inserted too far into a patient's rectum. As the cannula is inserted to its maximum penetration depth, the upper surface 27a of the radially-extending flange abuts the patient's anus and prevents inadvertent over-penetration. It is clear that the radially-extending flange does not need to extend around the entire circumference of the cannula in order to perform this function. Any radially-extending projection that hinders passage of the cannula through the anus may be used if over-penetration is a concern.

A lower surface 27b of the radially-extending flange 27a may act as a lug that allows a user to apply an insertion-force in the direction of the distal end 26 of the cannula to facilitate its insertion.

The proximal end 25 of the cannula body 23 defines an internal cavity 28 in which a threaded linkage is pressed so as to allow the cannula to be coupled to a source of driving fluid (e.g. liquid). The thread is compatible with luer fittings as are well known in the medical profession. Luer fittings are commonly used to attach tubing and syringes and needles for medical use.

The internal surface of the cavity 22 is substantially cylindrical in cross-section and does not comprise any sudden changes in cross-section in order to minimise turbulence when a liquid is forced through the cavity 22.

In use, a pharmaceutical composition comprising activated carbon particles is contained within the cavity 22.

The pharmaceutical composition comprises about 1.2 g activated carbon (e.g. 1 g in Example 3 below) of average particle size 0.15 mm to 0.3 mm wherein 85% or more of the activated carbon particles have diameter in the range from 0.152 mm to 0.297 mm. The activated carbon is obtained from Chemviron Carbon tested to EUP 2010 Version 7.

The cavity 22 and the distal opening 24 are sized and shaped to optimise delivery of activated carbon particles having an average particle size of between 0.15 mm and 0.3 mm. Particles of this size range are easier to handle compared with fine activated carbon particles previously used for medical treatments and do not stick or agglomerate within the cavity to a great extent, which would hinder their delivery. As the particles are loaded within an elongated cavity that has a wide opening, the water entering the cavity through the one-way valve effectively acts to push the particles out of this opening. Preferably the water does not mix with the particles within the cavity (although some mixing is inevitable) but rather the front of the water entering through the valve pushes the cavity full of activated carbon particles ahead of it.

When loaded within the cavity 22, the activated carbon particles are prevented from escaping through the proximal opening 21 by means of the one-way valve 50 that spans the proximal opening. The distal opening 24 may also be closed by a closure means in order to retain the particles within the cavity 22. For example, the device may comprise a removable seal or a frangible seal spanning the distal opening 24. Alternatively or additionally, the device may comprise a cap that acts to close the distal opening 24 and, thereby retain any pharmaceutical composition within the cavity 22 until it is desired to use the device.

The cannula body is formed by an injection moulding process from a medical grade polyethylene. Polyethylene is a substantially inert material that is commonly used in medical devices. It is noted that the cannula may be formed from any suitable medical material and that the person skilled in the art would be aware of such material. For example the cannula may be made from a polyethylene, polupropylene or a polycarbonate or some other convenient medical grade polymer.

The syringe is a standard syringe having a liquid capacity of 12 ml, and comprises a plunger 31 that is slidable within a barrel 32. The syringe has a threaded luer-type connection 33, which allows the syringe to be coupled to the flexible tubing 40. The syringe acts as an actuation means of the device for driving a volume of liquid through the cannula cavity 22 to flush a dose of pharmaceutical composition contained within the cannula cavity.

The flexible tubing 40 is formed from a flexible medical-grade polyvinyl chloride (PVC) and has an internal diameter of 2.6 mm, a length of 45 cm, and a capacity (i.e. the volume defined by the lumen of the tubing) of 2.4 ml. Each end of the flexible tubing terminates in a luer-type connection 41, 42. A first luer connection 41 allows the flexible tubing to be connected to the proximal end of the cannula 20 while a second luer connection 42, at the opposite end of the flexible tubing to the first luer connection 41, allows the flexible tubing to be connected to the syringe 30.

Figure 4:
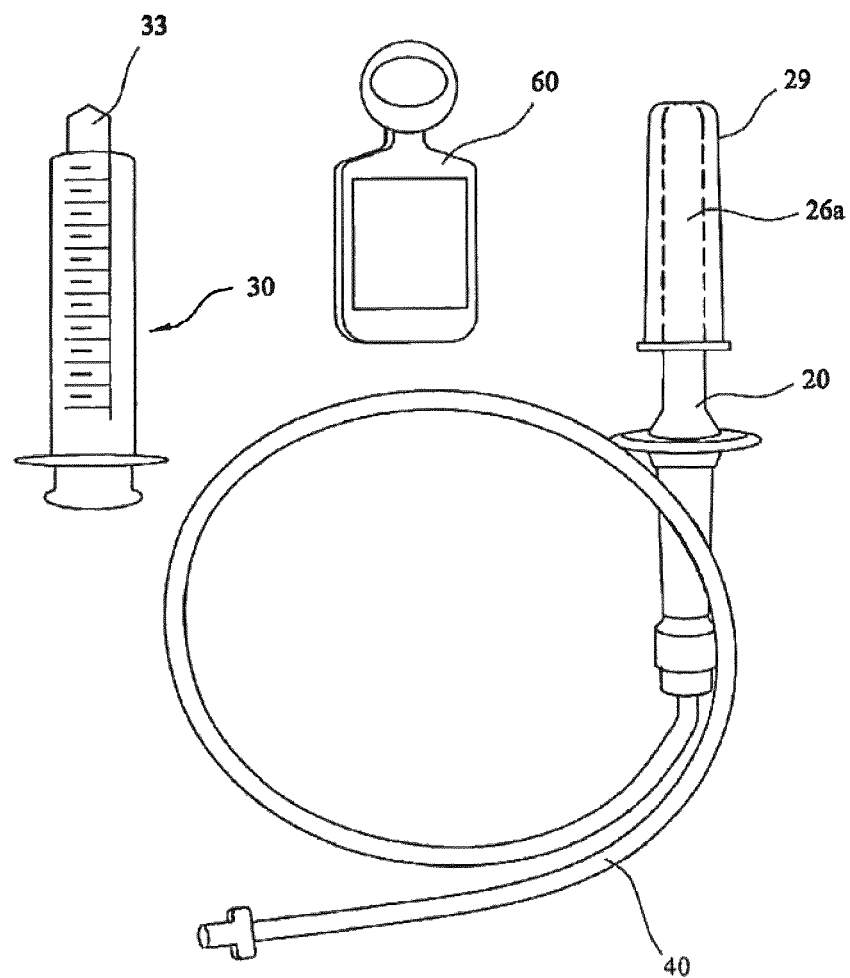
FIG. 4 illustrates a kit of parts for the treatment of pouchitis and proctitis comprising a device according to the embodiment of FIG. 1 and a source of sterile water.

It may be particularly convenient to supply a patient with both the device and any further elements that they need to self-administer a dose of a pharmaceutical composition comprising activated carbon particles. Thus, it may be advantageous to supply component elements of a device for delivering a dose of pharmaceutical composition and other materials in the form of a kit. An embodiment of such a kit is illustrated in FIG. 4. This kit includes component parts of a device as described above, i.e. a rectally insertable cannula 20, a syringe 30, and a length of flexible tubing 40 for connecting the syringe to the cannula (the flexible tubing is shown connected to the cannula). The kit also comprises a container filled with water for injection 60. The water for injection is used as a driving fluid to expel the pharmaceutical composition through the cannula and into the patient.

The kit may comprise other components. For example, the kit may include a supply of activated carbon for loading into the cannula. The kit may comprise a plurality of cannulas, each one pre-loaded with a dose of activated carbon.

In FIGS. 3 and 4, the cannula 20 is shown with its distal portion 26a sheathed within a cap 29. The cap comprises a stopper or bung 29a and a downwardly depending sheath 29b, and both sheaths the distal portion of the cannula 26a and closes the distal opening 24 thereby retaining medicament within the cannula.

The cannula is supplied pre-loaded with a pharmaceutical composition consisting of particles of activated carbon. The kit illustrated in FIG. 4 may be used to deliver a dose of a pharmaceutical composition comprising activated carbon particles as described below.

Figures 5, 6:
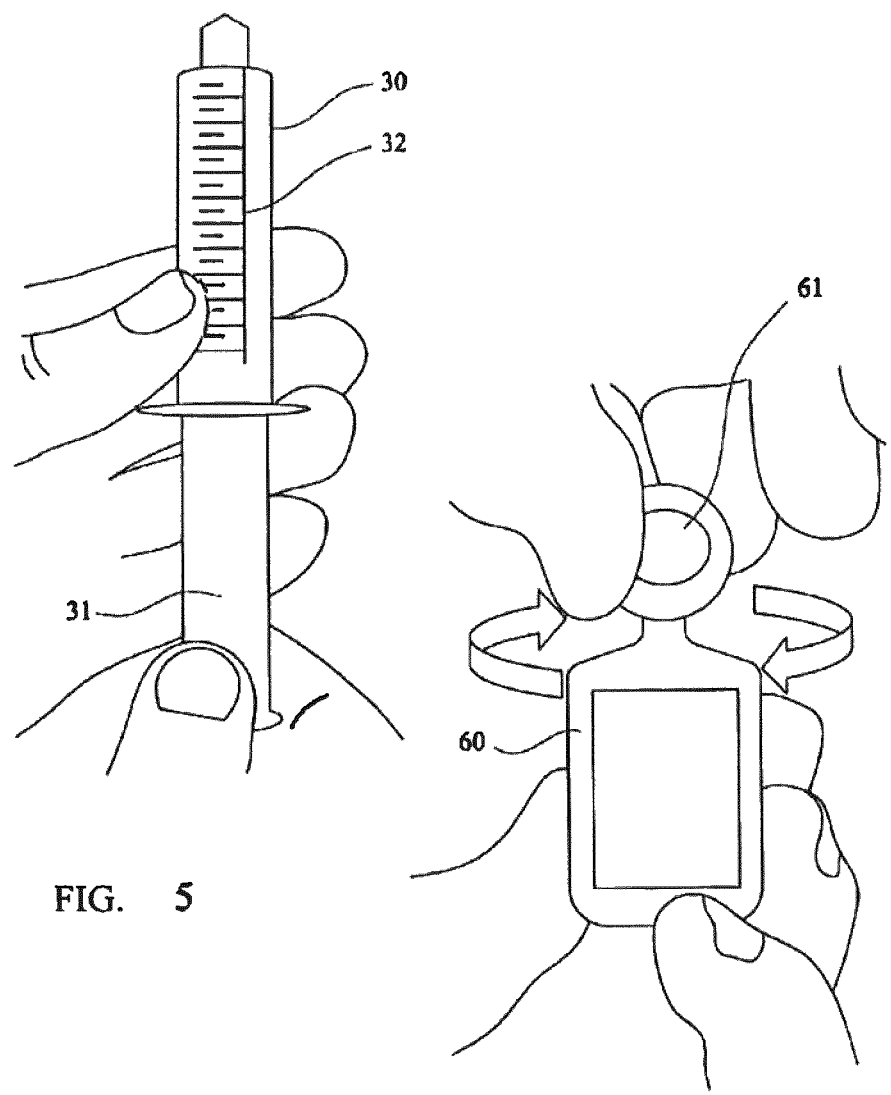
FIGS. 5 to 10 illustrate method steps involved in using the kit of FIG. 4.
Figure 7:
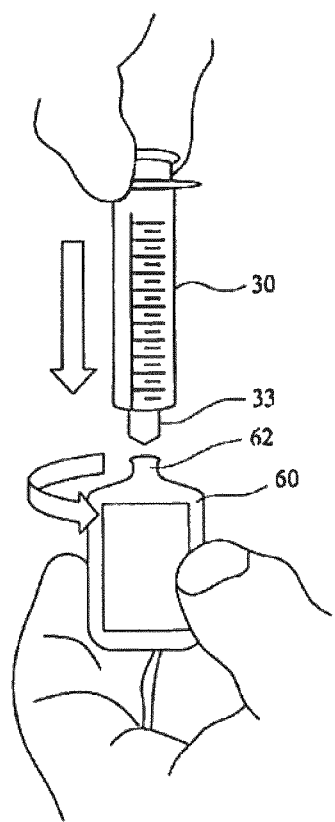

FIGS. 5 to 10 illustrate a method of using the kit as illustrated in FIG. 4 in order to deliver a dose of activated carbon particles. The individual component parts of the kit are removed from packaging in which they are supplied and set out before the user. The plunger 31 of the syringe 30 is withdrawn to the 11 ml marking on the barrel 32 of the syringe (as illustrated in FIG. 5). The user then removes a sealing cork 61 that acts to seal the container of water for injection 60 (illustrated in FIG. 6). The container of water 60 is maintained in an upright position so that its contents are not spilled.

The syringe 30 is coupled to the water container 60 in order to charge the syringe with water. The threaded luer connection 33 of the syringe engages with a corresponding mating thread in the neck 62 of the water container 60 (illustrated in FIG. 7).

Figure 8:
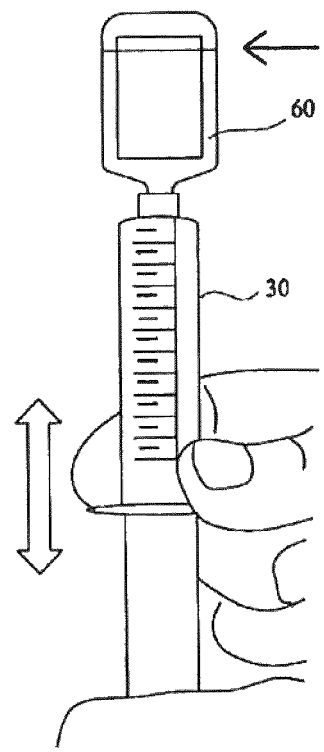
Figure 9:
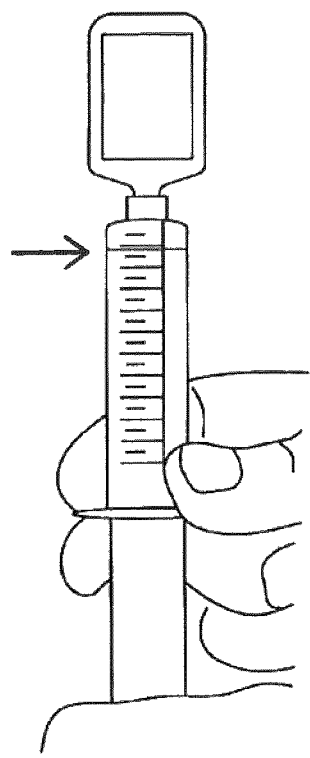

The water container 60, with the syringe now affixed, is inverted (illustrated in FIG. 8). The plunger 31 of the syringe 30 is then depressed to the 3 mm mark. This action causes air within the barrel of the syringe to be forced into the water container 60, which pressurises the container. The plunger is then withdrawn again. On withdrawal of the plunger, the water for injection passes into the barrel of the syringe. If required, the plunger can be repeatedly depressed and withdrawn. After these steps the barrel of the syringe should be filled with water for injection from the container of water 60 (this is illustrated in FIG. 9). Clearly, any technique for filling the syringe with the water may be used.

Figure 10:
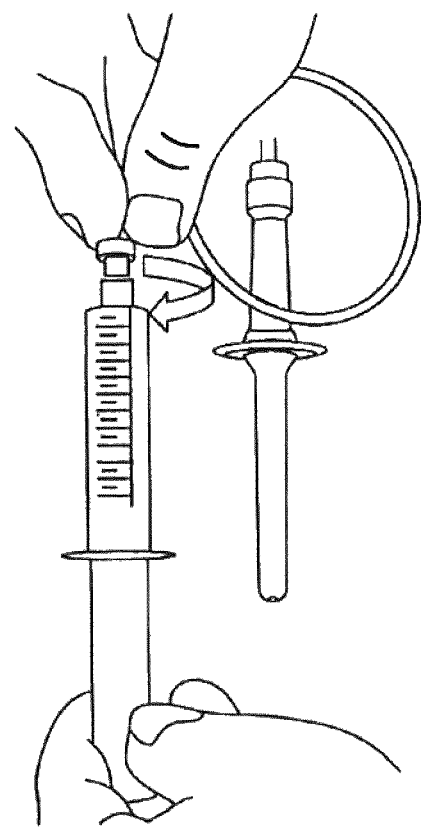

The cannula 20, which is preloaded with the pharmaceutical composition as described above, is coupled to the flexible tubing by screwing in the luer connections on the flexible tubing with equivalent connections on the cannula. Likewise, the flexible tubing is also connected to the syringe filled with water by coupling the luer connections on the flexible tubing and on the syringe (FIG. 10).

Immediately prior to use the cover or cap 29 is removed from the cannula 20. This opens the distal opening 24 such that the pharmaceutical composition can be forced out. If desired, the external surfaces of the distal portion 26a of the cannula may be lubricated, for example with petroleum jelly. Such lubrication may improve a patient's comfort on inserting the cannula. In some embodiments the distal portion of the cannula may be pre-lubricated. The distal portion 26a of the cannula 20 is then inserted carefully through the patient's anus so that the distal end 26 and the distal opening 24 enter the patient's rectal cavity. The cannula should be inserted until the radially-extending flange 27 abuts the anus and prevents further insertion.

With the cannula in place, the plunger 31 of the syringe 30 is pressed quickly. The plunger should preferably travel to its full extent over a period of no longer than 2 seconds. The water for injection contained within the barrel of the syringe is forced out of the syringe and through the flexible tubing 40, through the one-way valve 50 that closes the proximal opening 21 of the cannula and into the cannula cavity. On entering the cannula cavity 22, the flow of water forces the pharmaceutical composition that is contained within the cavity out of the cavity through the distal opening 24 and into the patient's rectal cavity.

After delivery of the pharmaceutical composition the cannula is removed from the patient's rectum. The cannula may then be cleaned, if it is to be re-used, or disposed of, if the device is only intended for one-time-use.

The device, kit, and method of using the device and kit as described herein refer to a specific embodiment. It is clear that many factors may be varied without changing the nature of the invention. For example, the embodiment described in detail above utilises a syringe as an actuation means for driving a volume of liquid through the cannula cavity. Any suitable actuation means may be used instead. For example, it may be possible to use a bellows or a bulb as an alternative to a syringe. In particular, it may be possible to replace the syringe with an automatic or motorised injection means for driving the volume of liquid.

The actual volume of liquid injected, and therefore the size of the syringe, may be varied. For example, such variation may be desirable if the volume of the cannula cavity is larger or smaller than the embodiment described above, or if the length of flexible tubing is longer or shorter. The volume of liquid should be sufficient to drive the entire contents of the cannula into the patient's rectum without delivering an excessive volume of liquid to the patient.

Although the embodiment described above uses flexible tubing disposed between the syringe and the cannula, other embodiments may dispense with the flexible tubing and provide a direct connection between the cannula and syringe or other means for driving the volume of liquid.

The size and shape of the cannula may be varied from the dimensions described in the embodiment above. Different sized cannulas may, for example, allow different volumes of pharmaceutical composition to be dispensed to a patient.

As set out above, the applicants have found that if the activated carbon is of particle size 0.15 mm to 1 mm, a liquid (e.g. water) should be used as driving fluid to deliver the dry powder. The applicants have surprisingly found that if the activated carbon is of particle size 0.05 mm to 0.15 mm, the fluid (driving fluid) may be either a liquid (e.g. water, as above) or a gas (e.g. air).

Herein, particle sizes are expressed, where appropriate, as the volume mean diameter (VMD). The volume mean diameter of the microparticles is well known and is readily measured by techniques known in the art.

Example 2 Oral Formulation

As set out above, it is possible to use an oral formulation to treat proctitis and pouchities. A suitable oral formulation is described as follows.

Activated carbon particles made from coconut shells are milled down to granules of particle size 0.2 mm to 2.0 mm). These individual particles (granules) are each coated with an inner coating (insoluble semipermeable membrane) comprising a mixture of Eudragit RS 30 D and Eudragit RL 30 D, which is applied by methods well known in the art (e.g. the methods of U.S. Pat. No. 6,632,454 B2). The individual coated activated carbon particles (granules) are then each coated with an outer enteric coating comprising Eudragit FS 30 D, again by methods well known in the art (e.g. the methods of U.S. Pat. No. 6,632,454 B2), to provide an oral formulation.

The oral formulation is suitable for oral administration e.g. as a powder or suspension to treat proctitis or pouchitis. In another example the coated particles (granules) may be formulated as a tablet or in a capsule.

Example 2A The Components of the Oral Composition

The oral composition (e.g. pharmaceutical composition) of the invention comprises:

(a) a core comprising activated carbon (e.g. activated carbon as the sole active pharmaceutical ingredient);

(b) a first (e.g. an inner) layer around (e.g. surrounding) the core, the first layer comprising an insoluble semipermeable material; and (c) a second (e.g. outer) layer around (e.g. surrounding) the first layer which breaks down rapidly (dissolves) at a predetermined pH (e.g. a layer which breaks down rapidly (dissolves) at pH 5 to pH 7) or which dissolves at a predetermined location in the gastrointestinal tract.

The following deals with each layer in turn.

(a) A Core Comprising Activated Carbon

Activated Carbon and its Production

To ensure the suitability of the activated carbon starting material for processing into a final uniform and reproducible product, the activated carbon starting material is subjected to a pre-treatment process. The objective of this pre-treatment is to reduce the number of burrs, tips and sharp edges because these will negatively impact the quality of the first (and second) layers which are applied to the surface of the activated carbon. A burr, tip or sharp edge is more difficult to cover with a uniform layer of coating material, hence particles are subjected to mechanical erosion to form a more uniform surface.

The starting material activated carbon is made from coconut shells (Chemviron Carbon, Lockett Road, Ashton-In-Makerfield, Lancashire WN4 8DE UK product name AQUACARB 607C 14×40 having a particle size from 1.40 mm to 0.425 mm). The process mechanically erodes burrs, tips or edges on the individual carbon particles by having them colliding with one another at high speed when passing through a collision tube, followed by a sieving process to achieve particles of adequate size distribution. After completing the erosion process, the collected particles are now subjected to a vibration sieve in portions of 200 g and sieved through a 1.0 and subsequently a 0.6 mm sieve. The fraction passing the 1.0 mm sieve and not the 0.6 mm sieve has an acceptable particle size and shape to be used as starting material for coating processes.

(b) the First Layer Around the Core, the First Layer Comprising an Insoluble Semipermeable Material:

It was a target to develop film compositions with a minimum of additives (especially for the inner film) to minimise take up of adsorptive capacity by additives. The first (e.g. an inner) layer may therefore consist essentially of the insoluble semipermeable material (e.g. ethyl cellulose) and (optionally) the water soluble material (e.g. HPMC). Avoiding other ingredients/excipients prevents loss of adsorptive capacity of the activated carbon to these excipients. The simplest film would be an ethylcellulose film (insoluble semipermeable material alone) applied from an ethanol solution. It was expected that this film would be very tight, not allowing sufficient/efficient passage of unwanted substances. Thus, to ensure that the adsorption capacity of activated carbon is made available/accessible, different water soluble materials (e.g. water soluble polymers) were mixed into the ethylcellulose to make holes in it or make it dissolve (on exposure to the pH in the lower intestine/colon). Polyvinylpyrrolidone (PVP), Hypromellose (HPMC) and Polyvinyl alcohol (PVA) were used as water soluble polymers. PVP is both soluble in water at ethanol, HPMC only in water. Low viscosity grades of PVP and HPMC were chosen (Kollidon K30 and Pharmacoat 603 respectively) in order not to influence the coating process with highly viscous film solutions.

For the following examples, the film coating was performed by methods well known in the art, in a GEA Aeromatic Fielder Strea 1 fluid-bed installed with a wurster tube. Liquid was pumped with a peristaltic pump. As Hypromellose (HPMC) is not soluble in Ethanol and Ethylcellulose is not soluble in water, the ethanol/water mix at which both polymers can dissolve was found to be between 70:30 and 80:20. The mix 75:25 was chosen as standard in the film (first layer) formulations with Ethylcellulose combined with Hypromellose.

The first layer was added by the above methods, to provide compositions according to the invention as set out in the Tables below.

(c) the Second Layer Around the First Layer which Dissolves at a Predetermined PH and/or which Dissolves at a Predetermined Location in the Gastrointestinal Tract:

For the enteric coating, a polymer with release at higher pH was selected, aiming at having the activated carbon available as close to the colon as possible. On the other hand, choosing an enteric coating with release at a too high pH could mean that the activated carbon would not be available in all patients (because gut pH and transit time can vary considerably from patient to patient and day to day). Based on this, Aqoat HG (HPMC-AS; Hypromellose-Acetate-Succinate; releases at pH 6.5) was chosen for the examples. Alternatives could be e.g. other Aqoat products (which release at other pH values), mixtures of Eudragit S 100/FS 30 D and Eudragit L 100 to reduce the release from pH 7.0 resulting from using Eudragit S 100/FS 30 D alone.

The amount of enteric layer in the following examples is 8 to 16% w/w of the total composition, for example 10 to 14% w/w of the total composition, for example 12% w/w of the total composition.

For the following examples, the film coating was performed by methods well known in the art, in a GEA Aeromatic Fielder Strea 1 fluid-bed installed with a wurster tube. Liquid was pumped with a peristaltic pump.

The second layer was added by the above methods, to provide compositions according to the invention as set out in the Tables below.

Production of Compositions of the Invention

Compositions according to the invention were made according to the following Tables, in 300 g batches (i.e. 300 g activated carbon):

| Batch | Core | First layer | Second layer |
|---|---|---|---|
| RD1202-19-C2 | Activated carbon Sanded/deburred | 90% ethylcellulose, 10% HPMC Weight increase (thickness) 4% | Aquoat HG Weight increase (thickness) 8% |
| RD1202-22-C2 | Activated carbon Sanded/deburred | 90% ethylcellulose, 10% HPMC Weight increase (thickness) 6% | Aquoat HG Weight increase (thickness) 8% |
| RD1202-23-C2 | Activated carbon Raw (not sanded) | 90% ethylcellulose, 10% HPMC Weight increase (thickness) 4% | Aquoat HG Weight increase (thickness) 8% |

RD1202-19-C2 and RD1202-22-C2 are compositions of the invention and were based on sanded/deburred activated carbon produced by the method described above. The purpose of the sanding process was to round the corner of the activated carbon crystals to allow for the layers/films to cover the corners. Non-sanded activated carbon has very sharp and apex corners which would be considered difficult to cover uniformly during film coating. RD1202-23-C2 used raw and un-sanded activated carbon. The sanded activated carbon for all batches was fractionated by particle size and only the fraction 0.6 mm to 1.2 mm was used. However, it was subsequently decided that the fraction 0.6 mm to 1.0 mm is preferred.

The first layer for the examples in the Table was 90% ethylcellulose, 10% HPMC, and was applied in ethanol/water by the film coating process described above. The film coating processes all performed well in the STREA fluid-bed without the need for adding plastizicer. Inlet air temperature setpoint for the ethanol:water films was 33° C. Batches were removed after 4% (RD1202-19-C2, RD1202-23-C2) or 6% (RD1202-19-C2) theoretical weight increase.

The second enteric layer was applied to the first layer, also by methods described above. The enteric polymer was Hypromellose-Acetate-Succinate (HPMC-AS; Aqoat HG) dissolving at pH 6.5. Aqoat HG was designed for organic coating (ethanol/water mixture) and can be applied without the addition of plasticizers or lubricants. As the composition was already film coated using organic coatings, organic coating was used. The second layer film was formulated as a 6% solution in ethanol/water 80:20 and applied until 8% weight increase.

More information is given in the following Table:

| | | Batch no | | |
|---|---|---|---|---|
| | | RD1202-19 | RD1202-22 | RD1202-23 | |
| Inner film | Ethylcellulose (Ethocel 7) | 90% | 90% | 90% | — |
| | Hypromellose (HPMC: Pharmacoat 603) | 10% | 10% | 10% | — |
| | Activated charcoal | Sanded | Sanded | Raw | Sanded |
| | % increase in weight | 4% | 6% | 4% | 0% |
| | Ethanol 96% | 75% | 75% | 75% | — |
| | Purified Water | 25% | 25% | 25% | — |

| | | Batch no | | | |
|---|---|---|---|---|---|
| | | KD1202-19-C2 | RD1202-22-C2 | RD1202-23-C2 | RD1202-24 |
| Enteric coat | Hypromellose-AS (Aqoat HG) | 100% | 100% | 100% | 100% |
| | % increase in weight | 8% | 8% | 8% | 8% |
| | Ethanol 96% | 80% | 80% | 80% | 80% |
| | Purified Water | 20% | 20% | 20% | 20% |

The oral formulation is suitable for oral administration e.g. as a powder or suspension to treat proctitis or pouchitis. In another example the coated particles (granules) may be formulated as a tablet or in a capsule.

Example 3 Activated Charcoal as Treatment of Pouchitis or Radiation Proctitis, a Pilot Study (Clinical Phase: II)

Background:

The main pathophysiologic driver of many gastrointestinal disorders/diseases has been postulated to be translocation, i.e. the gastrointestinal mucosa has become leaky and substances that in normal situations should be kept in the lumen of the gut may pass across the gut epithelium. For example, patients who have undergone an IPAA (Ileal Pouch Anal Anastomisis) may develop an inflammation in the pouch mucosa, or pouchitis. It has been postulated that the inflammation is due to a decreased barrier function of the pouch mucosa, thus allowing for translocation. Similarly, proctitis is believed to be due to decreased barrier function.

It is feasible to assume that the two mentioned conditions may act as models for several other diseases in which decreased mucosal barrier function has been suggested as a pathophysiologic mechanism.

Objective:

To demonstrate that treatment of pouchitis and/or radiation proctitis with activated charcoal diminish the symptoms of the mucosal inflammation in these conditions.

The inclusion and exclusion criteria for the trial were as follows:

Inclusion: —Male or female above 18 years of age
—Acute pouchitis or Chronic Radiation Proctitis
—If radiation proctitis radiation should have been directed against the rectal area only
—Willing to undergo endoscopic examination
—Ongoing Inflammation as judged by investigator
—Diagnosis verified by histopathology
—No ongoing antibiotic treatment for the condition Exclusion: —Age below 18 years of age
—Relapsing pouchitis
—Signs of inflammation above the pouch
—Radiation directed to other parts of the intestines Background The activated carbon was administered using the device described above and illustrated in the attached Figures.

The dose administered by the medical device in the trial was 1 g. In order to provide as much activated carbon to the affected areas as possible the device was used twice daily (with at least 6 hours in between administrations); thus, the device was used to administer activated carbon at a dose of 1 g twice daily. The duration of the trial was 4 weeks.

The dose was administered by the patient in the morning: after breakfast (after defecation), and in the evening, prior to "going to bed".

Endpoints

A reduction in the number of stools per day was selected as the primary endpoint. Typically, a patient with proctitis or pouchitis will pass 10 to 12 stools. Secondary endpoints were reduction in pouch mucosal inflammation as judged at endoscopy; reduction in inflammatory response as judged by histopathology; reduction in severity of "urgency"; reduction in number of bloody stools; and reduction in severity of abdominal cramping. The Investigational Medical Device (IMD) is illustrated in the attached drawings (see especially FIGS. 1 and 4) and consisted of:

1. Rectal cannula set
   a. Rectal cannula with cap, valve and carbon chamber
   b. Connection tube with female connector
   c. Vaseline plug (soft yellow paraffin/vaselinum flavum)
   d. Activated carbon 1.3 g (for injection into the rectum)
2. Sterile water (Ph. Eur. Quality) 10 ml in plastic container
3. Sterile syringe (CE-marked)—10 ml All medical devices are provided by Nordic Drugs AB. Subjects were trained in the use of the device (i.e. in the manner described above with reference to the Figures) by the investigator or a nurse. The activated carbon (Activated Carbon 610C (EUP 2010) was administered using 10 ml. sterile water (Fresenius Kabi) by means of a sterile syringe (BRAUN Injekt, CE marked), by the method described above.

All medicinal device components were handled according to the principles of Good Manufacturing Practice and applicable ISO guidelines.

On day 1, consent was obtained and the patient instructed in how to use the device. The investigator performed an overall assessment of the patient's state of health in order to confirm eligibility.

The invention claimed is:

1. A method for treating a condition selected from the group consisting of proctitis, radiation proctitis, and pouchitis in a subject in need thereof, comprising administering to the subject an effective amount of a composition comprising activated carbon, wherein the method comprises orally administering an effective amount of a composition comprising:
   (a) a core consisting of activated carbon;
   (b) a first layer that provides an insoluble semipermeable membrane around the core, the first layer comprising a semipermeable material which is insoluble in water; and
   (c) a second layer around the first layer which breaks down rapidly at pH 5 to 7 and/or which dissolves at a predetermined location in the gastrointestinal tract.

2. A method according to claim 1, wherein the activated carbon has a particle size of from 0.001 to 1 mm.

3. A method according to claim 1, wherein the activated carbon has a particle size of from 0.02 to 1 mm.

4. A method according to claim 1, wherein the activated carbon has a particle size of from 0.05 mm to 1 mm.

5. A method according to claim 1, wherein the activated carbon has a particle size of from 0.02 to 5.0 mm.

6. A method according to claim 1, wherein the activated carbon has a particle size of from 0.6 to 1.2 mm.

7. A method according to claim 1, wherein the activated carbon has an average particle size of from 0.2 mm to 0.3 mm.

8. A method according to claim 1, wherein the activated carbon has an average particle size of from 0.15 mm to 1 mm.

9. A method according to claim 1, wherein the activated carbon has an average particle size of from 0.15 mm to 0.3 mm.

10. A method according to claim 1, wherein the composition comprises from 450 µg to 10 g activated carbon.

11. A method according to claim 1, comprising orally administering said composition comprising said core, said first layer around said core, and said second layer around said first layer, wherein said second layer dissolves at pH 5 to 7.

12. A method according to claim 11, wherein the insoluble semipermeable material of said first layer comprises one or more components selected from the group consisting of ethyl cellulose, glyceryl monostearate, cellulose acetate butyrate, dipolylactic acid, polyvinyl chloride, and a poly(meth)acrylate polymer.

13. A method according to claim 11, wherein said first layer further comprises a water soluble material.

14. A method according to claim 13, wherein said first layer further comprises a water soluble material comprising hydroxypropylmethyl cellulose (HPMC).

15. A method according to claim 13, wherein the water soluble material is mixed with the insoluble semipermeable material in said first layer.

16. A method according to claim 13, wherein the water soluble material is present in an amount of 0.1 to 30% by weight of the amount of the insoluble semipermeable material present in said first layer.

17. A method according to claim 13, wherein the water soluble material is present in an amount of 2 to 25% by weight of the amount of the insoluble semipermeable material present in said first layer.

18. A method according to claim 1, comprising orally administering said composition comprising said core, said first layer around said core, and said second layer around said first layer, wherein said second layer is an enteric layer comprising a material which remains substantially intact at pH 1 to 4.9, but which breaks down rapidly at pH 5 to 7.

19. A method according to claim 1, comprising orally administering said composition comprising said core, said first layer around said core, and said second layer around said first layer, wherein second layer comprises one or more components selected from the group consisting of hypromellose-acetate-succinate; cellulose acetate trimellitate (CAT); cellulose acetate phthalate (CAP); anionic copolymers based on methylacrylate, methylmethacrylate and methacrylic acid; hydroxypropyl methylcellulose phthalate (HPMCP); hydroxypropylmethylcellulose acetate succinate (HPMCAS); methacrylic acid and ethyl acrylate copolymers; methacrylic acid and methyl methacrylate copolymers at a 1:1 ratio; methacrylic acid and methyl methacrylate copolymers at a 1:2 ratio; polyvinyl acetate phthalate (PVAP), and shellac resins.

20. A method according to claim 1, wherein the activated carbon is the sole active pharmaceutical ingredient in said composition.

21. A method according to claim 1, comprising orally administering said composition comprising said core, said first layer around said core, and said second layer around said first layer, wherein said insoluble semipermeable material of said first layer comprises ethyl cellulose, and wherein said second layer comprises hydroxypropylmethylcellulose acetate succinate (HPMC AS).

22. A method according to claim 21, wherein said first layer further comprises a water soluble material comprising hydroxypropylmethylcellulose (HPMC).

23. A method for treating proctitis in a subject in need thereof, comprising rectally administering to the subject an effective amount of a pharmaceutical composition consisting of activated carbon.

* * * * *